United States Patent
Jafer et al.

(10) Patent No.: US 10,424,406 B2
(45) Date of Patent: Sep. 24, 2019

(54) METHODS AND SYSTEMS FOR WATERMARKING OF ANONYMIZED DATASETS

(71) Applicant: PRIVACY ANALYTICS INC., Ottawa (CA)

(72) Inventors: Yasser Jafer, Ottawa (CA); Khaled El Emam, Ottawa (CA)

(73) Assignee: PRIVACY ANALYTICS INC., Ottawa, ON (CA)

( * ) Notice: Subject to any disclaimer, the term of this patent is extended or adjusted under 35 U.S.C. 154(b) by 245 days.

(21) Appl. No.: 15/430,520

(22) Filed: Feb. 12, 2017

(65) Prior Publication Data

US 2018/0232488 A1    Aug. 16, 2018

(51) Int. Cl.
*H04L 29/06* (2006.01)
*G16H 10/60* (2018.01)
*G06F 21/62* (2013.01)
*G06F 16/215* (2019.01)

(52) U.S. Cl.
CPC .......... *G16H 10/60* (2018.01); *G06F 16/215* (2019.01); *G06F 21/6254* (2013.01)

(58) Field of Classification Search
CPC .. G06F 17/3012; G06F 21/6254; G06F 21/10; H04N 21/8358
USPC ................. 726/26–30; 713/176, 181; 380/46
See application file for complete search history.

(56) References Cited

U.S. PATENT DOCUMENTS

| | | | | |
|---|---|---|---|---|
| 8,131,999 | B2* | 3/2012 | Kerschbaum | G06F 21/6254 380/277 |
| 8,850,583 | B1* | 9/2014 | Nelson | H04L 63/1433 380/44 |
| 9,087,215 | B2* | 7/2015 | LaFever | G06F 21/6254 |
| 9,251,320 | B2* | 2/2016 | Lee | G06F 21/10 |

(Continued)

OTHER PUBLICATIONS

Martin Scaiano, et al., "A unified framework for evaluating the risk of re-identification of text de-identification tools" Journal of Biomedical Informatics 63 (Jul. 15, 2016) 174-183 (10 pages total).

(Continued)

*Primary Examiner* — Hosuk Song
(74) *Attorney, Agent, or Firm* — John Maldjian; Maldjian Law Group LLC

(57) ABSTRACT

A method includes receiving an initial dataset. Each record of the initial dataset comprises a set of quasi-identifier attributes and a set of non-quasi-identifier attributes. A processor assigns a link identifier to each record and replaces each set of quasi-identifier attributes with a range to form a generalized set. The processor removes duplicate records based on identical generalized sets to generate de-duplicated records. The processor generates a randomized record by replacing the generalized set of each de-duplicated record with a corresponding set of random values. The processor passes the set of random values of each randomized record through multiple hash functions to generate multiple outputs. The multiple outputs are mapped to a Bloom filter. The processor forms a dataset by combining each randomized record with one or more sets of non-quasi-identifier attributes. The set of random values is a fingerprint for a corresponding record of the dataset.

20 Claims, 20 Drawing Sheets

(56) References Cited

U.S. PATENT DOCUMENTS 9,361,481 B2 * 6/2016 LaFever ............. G06F 21/6218

OTHER PUBLICATIONS

Pierangela Samarati, et al., "Generalizing Data to Provide Anonymity when Disclosing Information" Jun. 1, 1998 (15 pages total).
Adeel Anjum, et al., "BangA: An Efficient and Flexible Generalization-Based Algorithm for Privacy Preserving Data Publication" Computers 2017, 6, 1; Published: Jan. 4, 2017 (21 pages total).

* cited by examiner

Table 1A : Dataset 500

| LINK_ID | EC | LOS, AYEAR, BMONTH, BYEAR | Non-QI Attributes |
|---|---|---|---|
| 1 | EC1 | [8 - 14],[2005 - 2007],[1 - 6],[1940 - 1949] | ... |
| 2 | EC2 | [1 - 7],[2005 - 2007],[7 - 12],[1940 - 1949] | ... |
| 3 | EC1 | [8 - 14],[2005 - 2007],[1 - 6],[1940 - 1949] | ... |
| 4 | EC3 | [1 - 7],[2005 - 2007],[1 - 6],[1970 - 1979] | ... |
| 5 | EC3 | [1 -7],[2005 - 2007],[1 - 6],[1970 - 1979] | ... |
| 6 | EC3 | [1 - 7],[2005 - 2007],[1 - 6],[1970 - 1979] | ... |
| 7 | EC4 | [1 - 7],[2005 - 2007],[7 - 12],[1960 - 1969] | ... |
| 8 | EC3 | [1 - 7],[2005 - 2007],[ 1 - 6],[1970 - 1979] | ... |
| 9 | EC4 | [1 - 7],[2005 - 2007],[7 - 12],[1960 - 1969] | ... |
| 10 | EC4 | [1 - 7],[2005 - 2007],[7 - 12],[1960 - 1969] | ... |

FIG. 5

Table 1B: First Subset 602

| LINK_ID | EC | LOS, AYEAR, BMONTH, BYEAR |
|---|---|---|
| 1 | EC1 | [8 - 14],[2005 - 2007],[1 - 6],[1940 - 1949] |
| 2 | EC2 | [1 - 7],[2005 - 2007],[7 - 12],[1940 - 1949] |
| 3 | EC1 | [8 - 14],[2005 - 2007],[1 - 6],[1940 - 1949] |
| 4 | EC3 | [1 - 7],[2005 - 2007],[1 - 6],[1970 - 1979] |
| 5 | EC3 | [1 -7],[2005 - 2007],[1 - 6],[1970 - 1979] |
| 6 | EC3 | [1 - 7],[2005 - 2007],[1 - 6],[1970 - 1979] |
| 7 | EC4 | [1 - 7],[2005 - 2007],[7 - 12],[1960 - 1969] |
| 8 | EC3 | [1 - 7],[2005 - 2007],[ 1 - 6],[1970 - 1979] |
| 9 | EC4 | [1 - 7],[2005 - 2007],[7 - 12],[1960 - 1969] |
| 10 | EC4 | [1 - 7],[2005 - 2007],[7 - 12],[1960 - 1969] |

Table 1C: Second Subset 604

| LINK_ID | Non-QI Attributes |
|---|---|
| 1 | ... |
| 2 | ... |
| 3 | ... |
| 4 | ... |
| 5 | ... |
| 6 | ... |
| 7 | ... |
| 8 | ... |
| 9 | ... |
| 10 | ... |

FIG. 6

Table 1D: De-duplicated Dataset 702

| LINK_ID | LOS, AYEAR, BMONTH, BYEAR |
|---|---|
| 1,3 | [[8 - 14],[2005 - 2007],[1 - 6],[1940 - 1949] |
| 2 | [1 - 7],[2005 - 2007],[7 - 12],[1940 - 1949] |
| 4,5,6,8 | [1 - 7],[2005 - 2007],[1 - 6],[1970 - 1979] |
| 7,9,10 | [1 - 7],[2005 - 2007],[7 - 12],[1960 - 1969] |

FIG. 7

Table 1E: Randomized Dataset 802

| LINK_ID | LOS, AYEAR, BMONTH, BYEAR |
|---|---|
| 1,3 | 9, 2006, 4, 1942 |
| 2 | 6, 2005, 10, 1943 |
| 4,5,6,8 | 5, 2006, 3, 1971 |
| 7,9,10 | 2, 2005, 9, 1960 |

FIG. 8

Table 1F: Dataset 902

| LINK_ID | LOS, AYEAR, BMONTH, BYEAR | Non-QI Attributes |
|---|---|---|
| 1 | 9,2006,4,1942 | ... |
| 2 | 6,2005,10,1943 | ... |
| 3 | 9,2006,4,1942 | ... |
| 4 | 5, 2006, 3, 1971 | ... |
| 5 | 5, 2006, 3, 1971 | ... |
| 6 | 5, 2006, 3, 1971 | ... |
| 7 | 2, 2005, 9, 1960 | ... |
| 8 | 5, 2006, 3, 1971 | ... |
| 9 | 2, 2005, 9, 1960 | ... |
| 10 | 2, 2005, 9, 1960 | ... |

FIG. 9

Plot 1100

Number of verified records(x)

Table 11

| x | Pr(fp) = 0.1 | Pr(fp) = 0.03 | Pr(fp) = 0.02 | Pr(fp) = 0.01 |
|---|---|---|---|---|
| 1 | 0.1 | 0.03 | 0.02 | 0.01 |
| 2 | 0.01 | 0.0009 | 0.0004 | 0.0001 |
| 3 | 0.001 | 0.000027 | 0.000008 | 0.000001 |
| 4 | 0.0001 | 0.00000081 | 0.00000016 | 0.00000001 |
| 5 | 0.00001 | 2.43E-08 | 3.20E-09 | 1.00E-10 |
| 6 | 0.000001 | 7.29E-10 | 6.40E-11 | 1.00E-12 |
| 7 | 0.0000001 | 2.19E-11 | 1.28E-12 | 1.00E-14 |
| 8 | 0.00000001 | 6.56E-13 | 2.56E-14 | 1.00E-16 |
| 9 | 0.000000001 | 1.97E-14 | 5.12E-16 | 1.00E-18 |
| 10 | 1.00E-10 | 5.90E-16 | 1.02E-17 | 1.00E-20 |

Table 13A

| Variable | Description |
|---|---|
| BYEAR | Year of birth of a patient |
| BMONTH | Month of birth of a patient |
| LOS | Length of stay in the hospital |
| AYEAR | The year in which a patient was admitted |
| ZIP (only in DBB dataset) | ZIP code of patient |
| GENDER | The Gender of a patient |

Table 13B

| Variable | Generalization hierarchy |
|---|---|
| BYEAR | Years -> 5-year bins -> 10-year bins ->20-year bins |
| BMONTH | Months -> 3-month bins -> 4-month bins ->6-month bins |
| LOS | Days -> days up to six days, weeks afterwards -> less than a week; (1-2] weeks; (2-4] weeks; (4-8] weeks; (8-12 weeks]; (12-26] weeks -> Less than 4 weeks; (4-8] weeks; (8-12 weeks]; (12-26] weeks; greater than 26 weeks |
| AYEAR | Years -> 2-year bins -> 3-year bins -> 5-year bins |
| ZIP | [4 digits] -> [3 digits] -> [2 digits] -> [1 digit] |
| GENDER | Not Generalized |

FIG. 13

Table 15A

| Unique Combination(s) | Extracted From | Found in |
|---|---|---|
| 8,2008,10,2006 | DBA_AD3 | DBA_BF3 |
| 12,2008,8,1987 | DBA_AD3 | DBA_BF3 |
| 19,2008,1,2003 | DBA_AD95 | DBA_BF95 |
| 19,2007,8,1973 | DBA_AD95 | DBA_BF95 |
| 15,2007,7,1967<br>2,2007,11,1958 | DBA_AD95 | DBA_BF95 |
| 30,2008,7,2000<br>65,2008,5,1920 | DBA_AD35 | DBA_BF35 |
| 20,2004,7,2006 | DBA_AD35 | DBA_BF35DBA_BF21 |
| 20,2004,7,2006<br>19,2004,4,1988 | DBA_AD35 | DBA_BF35 |

Table 15B

| | |
|---|---|
| Time required to anonymize the DBA dataset using [A-B] generalization (single copy) | 1700 s |
| Average time required to Randomize a single dataset | 35 ms |
| Average time required to embed hash a single dataset into its Bloom filter | 5 ms |
| Time required to verify a complete dataset against 100 Bloom filters | 8 s |

FIG. 15

Table 17A

| Unique Combination(s) | Extracted From | Found in |
|---|---|---|
| 8,139,2008,8,1957 | DBB_AD74 | DBB_BF74 |
| 3,112,2008,4,1928 | DBB_AD74 | DBB_BF74 |
| 5,100,2008,7,2004 | DBB_AD14 | DBB_BF14DBB_BF69 |
| 5,100,2008,7,2004 1,144,2007,5,1975 | DBB_AD14 | DBB_BF14 |
| 4,122,2008,4,1915 | DBB_AD97 | DBB_BF97DBB_BF67 |
| 4,122,2008,4,1915 4,104,2008,5,2002 | DBB_AD97 | DBB_BF97 |

Table 17B

| | |
|---|---|
| Time required to anonymize the DBB dataset using [A-B] generalization (single copy) | 1500 s |
| Average time required to Randomize a single dataset | 300 ms |
| Average time required to embed hash a single dataset into its Bloom filter | 500 ms |
| Time required to verify a complete dataset against 100 Bloom filters | 40 s |

FIG. 17

Table 18

| Verified record | Bloom Filter B1 | Bloom Filter B6 |
|---|---|---|
| r' | Member | Non-member |
| r" | Non-member | Member |

FIG. 18

METHODS AND SYSTEMS FOR WATERMARKING OF ANONYMIZED DATASETS

FIELD OF THE INVENTION

The present invention relates to methods and systems for watermarking of anonymized datasets. More specifically, the present invention relates to embedding and verifying watermarks in multiple releases of anonymized datasets.

BACKGROUND

Electronic databases of patient health records are useful for both commercial and non-commercial purposes. The patient health records are typically collected from multiple sources in a variety of formats. For example, medical service providers supply individually identified patient transaction records to medical insurance industry for compensation. The patient transaction records, in addition to personal information data fields or attributes, may contain other information concerning, for example, diagnosis, prescriptions, treatment or outcome. Such information poses significant security and privacy problems. Therefore, to preserve individual privacy, it is important that the patient records integrated with a database facility are "anonymized" or "de-identified".

Another concern with sensitive datasets is unauthorized duplication, distribution and tampering after release of the datasets to one or more intended recipients. Digital watermarking can be used to determine the source of an unauthorized or illegally disseminated copy. For example, when a document is to be secured using digital watermarking, an identifier that identifies the customer who is to receive the electronic distribution copy of the document can be imperceptibly embedded in the document, along with the copyright holder's watermark. Further, the main application of watermarking a relational database includes ownership assertion, fingerprinting, and fraud and tamper detection. For example, if a recipient of the database disseminates copies of the distribution copy contrary to the interests of the copyright holder, the recipient can be identified based on the digital watermark, which is present in all the unauthorized or illegally disseminated copies. However, when many distribution copies are disseminated legally to different recipients, individually linking each distribution copy to a specific recipient has typically proven to be difficult and time consuming.

Related art includes various schemes of fingerprinting individual records of a dataset intended to be released to multiple recipients. One such scheme includes query optimization for fingerprinting relational databases while satisfying usability constraints. However, such schemes may be susceptible to incorrect fingerprint detection following data tampering or an attack due to dependence of fingerprint decoding on usability constraints.

Related art also includes a K-anonymity process, which is a model for protecting privacy. This privacy model and process was proposed in order to prevent record linkage. A table is considered "K-anonymous" if quasi-identifier (QI) values of each record are indistinguishable from at least K−1 other records in the dataset. For example, if a record includes a QI value, there are at least K−1 other records that have the same QI value. The records that share the same QI value form an Equivalence Class (EC).

There is a requirement for watermarking and fingerprinting multiple releases of large datasets while preserving the quality of the datasets and linking each release to the corresponding recipient.

SUMMARY

A goal of embodiments is to use the generalization that is applied to the dataset for anonymization, for an additional purpose of fingerprinting. Embodiments achieve these objectives without injecting noise into the dataset, which would reduce the utility of the data. Anonymization both protects the privacy of individuals in the dataset, and incorporates efficient fingerprints in a release dataset. Embodiments achieve these objectives while allowing many releases of a large datasets. These release datasets need to be unique, having fingerprints built in, and to be anonymized.

Embodiments disclosed herein relate to systems and methods for fingerprinting a relational database to prevent unauthorized duplication and distribution of the database when the database is publicly available over a network.

Embodiments disclosed herein further provide systems and methods that utilize Bloom filters to embed and verify fingerprints in a large dataset. Utilization of the Bloom filters provides a fast mechanism for embedding and verifying fingerprinting. A size of each of the Bloom filters is appropriately selected based on the number of records in order to reduce computational load and memory storage, while ensuring an acceptable probability of false positives during verification.

Embodiments disclosed herein further provide systems and methods that embed watermarks in multiple releases of large anonymized datasets while linking each record with the intended recipient for detecting any unauthorized duplication, distribution and tampering.

Embodiments disclosed herein further provide systems and methods that embed watermarks and/or fingerprints in datasets without adding noise or impacting a quality of the datasets.

Embodiments disclosed herein further provide systems and methods that reduce computational load of embedding and verifying fingerprints in large datasets by de-duplicating generalized sets of Quasi-Identifier (QI) attributes. Further, each generalized set of QI attributes is replaced by a set of random values during each release of the dataset to link each release with a unique recipient.

Embodiments in accordance with the present invention are directed to a method of forming a watermarked and anonymized dataset to be released to a recipient. The method includes receiving an initial dataset comprising a plurality of records at a server. Each record comprises a set of quasi-identifier attributes and a set of non-quasi-identifier attributes. The server includes a processor and a memory. The processor assigns a link identifier to each record. The link identifier is unique for each record. The processor further replaces each quasi-identifier attribute value of the set of quasi-identifier attributes of each record with a range of values to form a generalized set. The range of values is based on a type of the corresponding quasi-identifier attribute and is determined by a k-anonymization process. The processor further partitions the initial dataset into a first subset and a second subset based on the set of quasi-identifier attributes and the set of non-quasi-identifier attributes of each record. Each generalized set representing each set of quasi-identifier attributes and the corresponding link identifier form a record of the first subset. Further, each set of non-quasi-identifier attributes and the corresponding link identifier form a record of the second subset. The processor removes duplicate records from the first subset to generate a plurality of de-duplicated records. The duplicate records are removed based on identical generalized sets. The processor further generates a set of random values corresponding to the generalized set of each de-duplicated record. Each random value lies within the range of values corresponding to each quasi-identifier. The processor generates a randomized record by replacing the generalized set of each de-duplicated record with the corresponding set of random values. Each randomized record further comprises one or more link identifiers corresponding to one or more records of the second subset. The processor passes the set of random values of each randomized record through a plurality of hash functions to generate a plurality of outputs. The plurality of outputs of the plurality of hash functions are mapped to a Bloom filter. The processor reconstructs the release dataset by combining each randomized record with one or more corresponding records of the second subset based on the one or more link identifiers. The set of random values of each randomized record is a fingerprint for the one or more corresponding records of the release dataset. Further, the release dataset is released to the recipient.

Embodiments in accordance with the present invention are further directed to a system for forming a release dataset for release to a recipient. The system comprises a server including a processor and a memory. The server receives an initial dataset comprising a plurality of records. Each record comprises a set of quasi-identifier attributes and a set of non-quasi-identifier attributes. The processor is configured to assign a link identifier to each record. The link identifier is unique for each record. The processor is further configured to replace each quasi-identifier attribute of the set of quasi-identifier attributes of each record with a range of values to form a generalized set. The range of values is based on a type of the corresponding quasi-identifier attribute. The processor also is configured to partition the initial dataset into a first subset and a second subset based on the set of quasi-identifier attributes and the set of non-quasi-identifier attributes of each record. Each generalized set representing each set of quasi-identifier attributes and the corresponding link identifier form a record of the first subset. Each set of non-quasi-identifier attributes and the corresponding link identifier form a record of the second subset. The processor is further configured to remove duplicate records from the first subset to generate a plurality of de-duplicated records. The duplicate records are removed based on identical generalized sets. The processor also is configured to generate a set of random values corresponding to the generalized set of each de-duplicated record. Each random value lies within the range of values corresponding to each quasi-identifier. The processor is further configured to generate a randomized record by replacing the generalized set of each de-duplicated record with the corresponding set of random values. Each randomized record further comprises one or more link identifiers corresponding to one or more records of the second subset. The processor also is configured to pass the set of random values of each randomized record through a plurality of hash functions to generate a plurality of outputs. The plurality of outputs of the plurality of hash functions are mapped to a Bloom filter. The processor is further configured to reconstruct the release dataset by combining each randomized record with one or more corresponding records of the second subset based on the one or more link identifiers. The set of random values of each randomized record is a fingerprint for the one or more corresponding records of the release dataset. Further, the release dataset is released to the recipient.

Embodiments in accordance with the present invention are further directed to a method of forming a plurality of release datasets for release to a plurality of recipients. The method includes receiving an initial dataset comprising a plurality of records at a server. Each record includes a set of quasi-identifier attributes and a set of non-quasi-identifier attributes. The server comprises a processor and a memory. The processor performs the following: (a) assigning a link identifier to each record, wherein the link identifier is unique for each record; (b) replacing each quasi-identifier attribute of the set of quasi-identifier attributes of each record with a range of values to form a generalized set, wherein the range of values is based on a type of the corresponding quasi-identifier attribute; (c) partitioning the initial dataset into a first subset and a second subset based on the set of quasi-identifier attributes and the set of non-quasi-identifier attributes of each record, wherein each generalized set representing each set of quasi-identifier attributes and the corresponding link identifier form a record of the first subset, and wherein each set of non-quasi-identifier attributes and the corresponding link identifier form a record of the second subset; (d) removing duplicate records from the first subset to generate a plurality of de-duplicated records, wherein the duplicate records are removed based on identical generalized sets; (e) generating a set of random values corresponding to the generalized set of each de-duplicated record, wherein each random value lies within the range of values corresponding to each quasi-identifier; (f) generating a randomized record by replacing the generalized set of each de-duplicated record with the corresponding set of random values, wherein each randomized record further comprises one or more link identifiers corresponding to one or more records of the second subset; (g) passing the set of random values of each randomized record through a plurality of hash functions to generate a plurality of outputs, wherein the plurality of outputs of the plurality of hash functions are mapped to a Bloom filter; (h) assigning the Bloom filter to a recipient of the plurality of recipients, wherein a unique Bloom filter is assigned to each recipient; (i) reconstructing a release dataset by combining each randomized record with one or more corresponding records of the second subset based on the one or more link identifiers, wherein the set of random values of each randomized record is a fingerprint for the one or more corresponding records of the released dataset; (j) repeating steps (e) to (h) to generate the plurality of release datasets for the plurality of recipients, wherein the plurality of release datasets are released to the plurality of recipients.

These and other advantages will be apparent from the present application of the embodiments described herein.

The preceding is a simplified summary to provide an understanding of some embodiments of the present disclosure. This summary is neither an extensive nor exhaustive overview of the present disclosure and its various embodiments. The summary presents selected concepts of the embodiments of the present disclosure in a simplified form as an introduction to the more detailed description presented below. As will be appreciated, other embodiments of the present disclosure are possible utilizing, alone or in combination, one or more of the features set forth above or described in detail below.

BRIEF DESCRIPTION OF THE DRAWINGS

The foregoing and other aspects of the embodiments disclosed herein are best understood from the following detailed description when read in connection with the accompanying drawings. For the purpose of illustrating the embodiments disclosed herein, there is shown in the drawings embodiments that are presently preferred, it being understood, however, that the embodiments disclosed herein are not limited to the specific instrumentalities disclosed. Included in the drawings are the following figures:

FIG. 5 illustrates an exemplary dataset, in accordance with an embodiment of the present disclosure;

FIG. 6 illustrates a first subset and a second subset, in accordance with an embodiment of the present disclosure;

FIG. 7 illustrates a de-duplicated dataset, in accordance with an embodiment of the present disclosure;

FIG. 8 illustrates a randomized dataset, in accordance with an embodiment of the present disclosure;

FIG. 9 illustrates a release dataset, in accordance with an embodiment of the present disclosure;

FIG. 13 illustrates a table containing a list of quasi-identifiers and a table containing a generalization hierarchy for the quasi-identifiers, in accordance with an embodiment of the present disclosure;

FIG. 15 illustrates a table containing verification results of a dataset and a table containing various times required for processing the dataset, in accordance with an embodiment of the present disclosure;

FIG. 17 illustrates a table containing verification results of a dataset and a table containing various times required for processing the dataset, in accordance with another embodiment of the present disclosure;

FIG. 18 illustrates a table containing an exemplary collusion detection, in accordance with an embodiment of the present disclosure;

Figure 1:
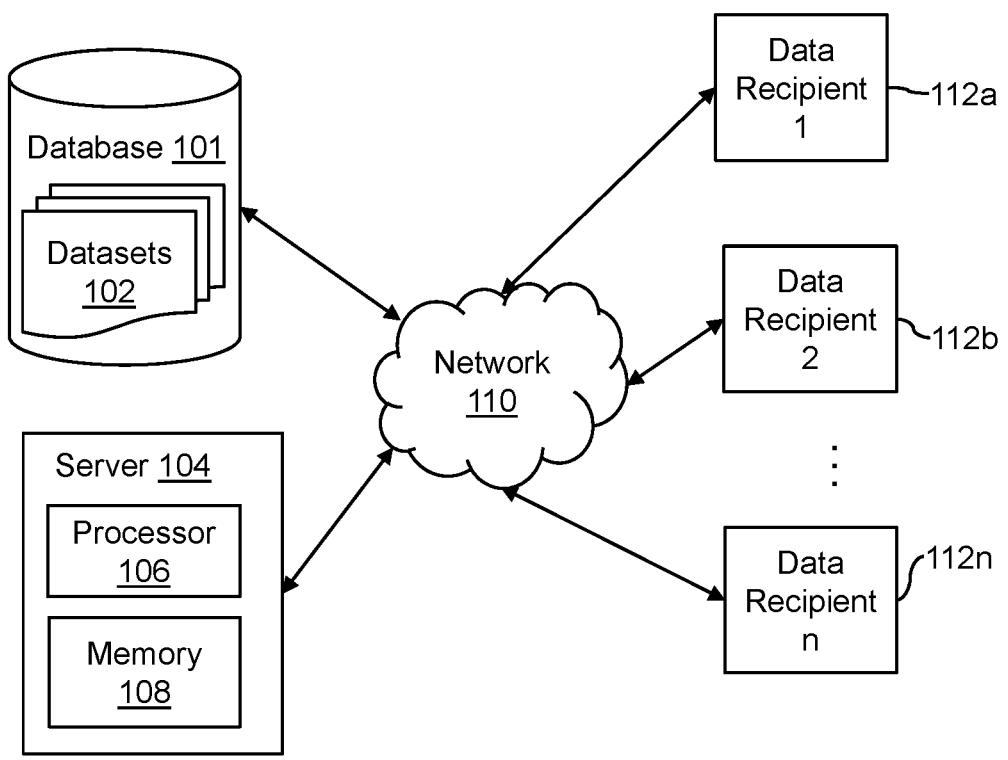
FIG. 1 illustrates a system for releasing a dataset, in accordance with an embodiment of the present disclosure.

While embodiments of the present disclosure are described herein by way of example using several illustrative drawings, those skilled in the art will recognize the present disclosure is not limited to the embodiments or drawings described. It should be understood the drawings and the detailed description thereto are not intended to limit the present disclosure to the form disclosed, but to the contrary, the present disclosure is to cover all modification, equivalents and alternatives falling within the spirit and scope of embodiments of the present disclosure as recited by the appended claims.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

DETAILED DESCRIPTION

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. The terms "comprising", "including", and "having" can be used interchangeably.

The term "dataset" refers to a collection of related sets of information that is composed of separate elements but can be manipulated as a unit by a computer.

Quasi-identifiers are pieces of information that are not of themselves unique identifiers, but are sufficiently well correlated with an entity that they can be combined with other quasi-identifiers to create a unique identifier. Quasi-identifiers can thus, when combined, become personally identifying information.

The term "watermark" refers to a type of information embedded into underlying data for the purposes of tamper detection, localization, ownership proof, and tracing a data recipient.

As used herein, the term "module" refers generally to a logical sequence of steps, processes or components. For example, a software module may comprise a set of associated routines or subroutines within a computer program. Alternatively, a module may comprise a substantially self-contained hardware device. A module may also comprise a logical set of processes irrespective of any software or hardware implementation.

A module that performs a function also may be referred to as being configured to perform the function, e.g., a data module that receives data also may be described as being configured to receive data. Configuration to perform a function may include, for example: providing and executing sets of computer code in a processor that performs the function; providing provisionable configuration parameters that control, limit, enable or disable capabilities of the module (e.g., setting a flag, setting permissions, setting threshold levels used at decision points, etc.); providing or removing a physical connection, such as a jumper to select an option, or to enable/disable an option; attaching a physical communication link; enabling a wireless communication link; providing electrical circuitry that is designed to perform the function without use of a processor, such as by use of discrete components and/or non-CPU integrated circuits; setting a value of an adjustable component (e.g., a tunable resistance or capacitance, etc.), energizing a circuit that performs the function (e.g., providing power to a transceiver circuit in order to receive data); providing the module in a physical size that inherently performs the function (e.g., an RF antenna whose gain and operating frequency range is determined or constrained by the physical size of the RF antenna, etc.), and so forth.

Fingerprinting is a type of watermark that identifies the recipient of a digital object as well as the owner of the digital object. Fingerprinting deters illegal redistribution by enabling the owner of the data object to identify the original recipient of the redistributed copy.

A Bloom filter is a data structure that is used to check for membership of an element in a set of elements. More specifically, a Bloom filter is known in the art as a space-efficient probabilistic data structure, used to test whether an element is a member of a set. False positive matches are possible, but false negatives are not. A query returns either "possibly in set" or "definitely not in set". Elements may be added to a set, but not removed from the set. Adding more elements to the set gives a larger probability of false positives unless the filter size is increased.

Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" or "server" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a Graphic Processing Unit (GPU), a FPGA (field programmable gate array), or an ASIC (application specific integrated circuit). In one example, a CUDA-based GPU may be used. In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a GPU, a FPGA (field programmable gate array), or an ASIC (application specific integrated circuit).

Computers suitable for the execution of a computer program include, by way of example, can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media (transitory or non-transitory, as appropriate) suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, processes, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

FIG. 1 illustrates a system 100 in accordance with the disclosed subject matter. The system 100 is configured to release one or more sets of a dataset to one or more recipients with a unique fingerprint embedded within each set. Specifically, the system 100 prevents unauthorized duplication and distribution of a dataset when the dataset is publicly available over a network. The system 100 includes a server 104 communicably coupled to a database 101.

The database 101 stores and maintains one or more datasets 102. In some embodiments, the dataset 102 may be a relational dataset. A relational database or a dataset is a collection of data items organized as a set of formally-described tables from which data can be accessed or reassembled in different ways without having to reorganize the database tables. The dataset 102 includes a plurality of records. Each record may include one or more fields containing information. For example, in case of a medical dataset, the record may include fields containing information of patients such as, but not limited to, name of patient, disease, length of stay, admission year, birth month, birth year and so forth. In some embodiments, each record may include a set of quasi-identifier attributes (hereinafter referred to as "QI attributes") and a set of non-Quasi-Identifier attributes (hereinafter referred to as "non-QI attributes"). In some embodiments, the dataset 102 may be anonymized based on the set of QI attributes. The non-QI attributes may be retained or may be replaced with a special character such as, but not limited to, "*", "$", and so forth. A good example where suppressing or replacing the values of non-QI attributes with special character is applicable is when these non-QI attributes are considered directed identifiers. In either case, non-QI attributes do not participate in the mechanism of fingerprint embedding or verification proposed in this invention. In some embodiments, the QI attributes may include information fields such as, but not limited to, length of stay (LOS), admission year (AYEAR), birth month (BMONTH) and birth year (BYEAR). Further, the set of non-QI attributes may include information fields such as, but not limited to, patient name, contact information, blood pressure, heart rate, and so forth. In the above examples of non-QIs, patient name and contact information are direct identifiers that may be replaced with special characters (e.g., "###"). However, blood pressure and heart rate may be retained since they are not distinguishable, replicable, or identifiable. In some embodiments, the database 101 may be stored in a memory device (not shown). Further, the memory device may include any memory device such as, but not limited to, a dynamic memory, a static memory, a hard drive, a flash memory, a cloud storage, and the like. The database 101 may be communicably coupled to the server 104 by a network 110. The network 110 can include any wired or wireless network that allows transfer of information. Though in the illustrated embodiment of FIG. 1, the database 101 is shown to be separate from the server 104, in alternative embodiments, the database 101 may be stored on the server 104.

The server 104 receives the dataset 102 from the database 101. The server 104 includes a processor 106 and a memory 108. The processor 106 performs a set of operations on the dataset 102 before final release to one or more of recipients 112a to 112n (hereinafter collectively referred to as "the recipients 112"). The set of operations may include generalization of the dataset 102, deduplication of the dataset 102, randomization of the dataset 102, and so forth.

The processor 106 may include any hardware for processing data, for example, but not limited to, one or more programmable processors, one or more computers, and so forth. The processor 106 can further include special purpose logic circuitry, e.g., a central processing unit (CPU), a FPGA (field programmable gate array), or an ASIC (application-specific integrated circuit). In some embodiments, the processor 106 may include a program code that creates an execution environment for computer programs, e.g., code that constitutes processor firmware, a protocol stack, a database management system, an operating system, or a combination of one or more of them. In some embodiments, the processor 106 may include an operating system.

The processor 106 may be communicably coupled to the memory 108 to perform the operations discussed herein. The memory 108 stores various information related to the dataset 102. The information can include link identifier associated with each record of the dataset 102, various filters associated with the dataset 102 and so forth. In some embodiments, the memory 108 also stores various data required for the operation of the processor 106. The data may include software, computer readable instructions, an operating system and so forth. The memory 108 may include any memory device such as, but not limited to, Random Access Memory (RAM), Read only memory (ROM), flash memory and so forth. Further, the server 104 may be communicably coupled to the data recipients 112 by the network 110.

The network 110 may include a data network such as, but not restricted to, the Internet, a local area network (LAN), a wide area network (WAN), a metropolitan area network (MAN), etc. In certain embodiments, the network 110 can include a wireless network, such as, but not restricted to, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS) etc. In some embodiments, the network 110 may include or otherwise cover networks or subnetworks, each of which may include, for example, a wired or wireless data pathway. The network 110 may further include a circuit-switched voice network, a packet-switched data network, or any other network capable for carrying electronic communications. For example, the network 110 may include networks based on the Internet protocol (IP) or asynchronous transfer mode (ATM), and may support voice usage, for example, VoIP, Voice-over-ATM, or other comparable protocols used for voice data communications. In one implementation, the network includes a cellular telephone network configured to enable exchange of text or SMS messages.

Examples of the network 110 may further include, but are not limited to, a personal area network (PAN), a storage area network (SAN), a home area network (HAN), a campus area network (CAN), a virtual private network (VPN), an enterprise private network (EPN), a global area network (GAN), and so forth. Embodiments may include an interface to substantially any type of network, including known, related art, and/or later developed technologies to connect the server 104, the database 101 and the data recipients 112.

The data recipients 112 may include any electronic device, such as desktop computers, portable computers, smartphones, tablet computers, wearable devices, and the like. The data recipients 112 may also include a display unit (not shown) for displaying any data. The display unit can include, but not limited to, a Cathode Ray Tube (CRT) display, a Liquid Crystal Display (LCD), a Light Emitting Diode (LED) display, and the like. Embodiments may include or otherwise cover any type of display, including known, related art, and/or later developed technologies. In some embodiments, the data recipients 112 are client side systems that wants a complete or a partial access to the dataset 102.

In an embodiment, the system 100 may utilize a Bloom filter for embedding and verifying watermarks or fingerprints in each record of the dataset 102.

Figure 2:
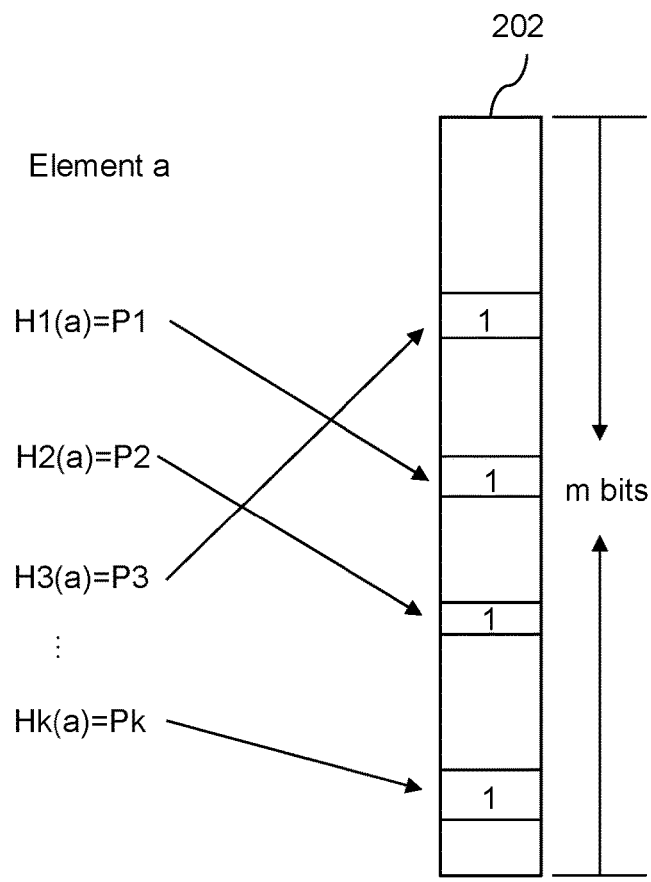
FIG. 2 illustrates a schematic representation of a Bloom filter, in accordance with an embodiment of the present disclosure.

FIG. 2 illustrates a schematic representation of a Bloom filter 200, in accordance with an embodiment of the present disclosure. In some embodiments, the Bloom filter 200 may be stored in the memory 108 (shown in FIG. 1). The Bloom filter 200 may include a bit vector array 202 (hereinafter referred to as "the array 202"). In some embodiments, a fingerprint may correspond to a plurality of bits of the array 202. In some other embodiments, one or more bits of the array 202 may be set to a value "1" to indicate an associated fingerprint. In an exemplary embodiment, the array 202 includes "m" bits. Initially, the processor 106 (shown in FIG. 1) may set each bit of the array 202 to a value "0". The Bloom filter 200 further includes a plurality of hash functions. For example, the Bloom filter 200 includes hash functions "H1" to "Hk". In an embodiment, "k" may be equal to 4. Each hash function is configured to take a value as an input and generate an output or a hash corresponding to the input. In some embodiments, the input to each of the hash functions is an element of a record of the dataset 102 (shown in FIG. 1). For example, the input to the hash functions "H1" to "Hk" is an element "a". The hash functions "H1" to "Hk" generate outputs "P1" to "Pk", respectively. Further, each of the outputs "P1" to "Pk" may correspond to a position in the array 202. As illustrated in FIG. 2, bits corresponding to the positions of the outputs "P1" to "Pk" are set to "1" to indicate association of the element "a" with the Bloom filter 200. Specifically, the bits at the positions H1(a), H2(a), . . . , Hk(a) in the array 202 are set to "1". Further, the hash functions "H1", to "Hk" provide same outputs, i.e., "P1" to "Pk" every time the element "a" is provided as an input. Therefore, the outputs "P1" to "Pk" act as an identifier for the element "a". In a similar manner, multiple elements may be provided as inputs to the Bloom filter 200 to form map a set of elements to the array 202. Further, the Bloom filter 200 may subsequently receive one or more queries to determine whether one or more elements are part of the set present in the array 202.

In an example, an element "b" is provided as a query for the hash functions "H1" to "Hk". The bits at the positions H1(b), H2(b), . . . , Hk(b) in the array 202 are checked. If any of the bits corresponding to the element "b" is "0", then the element "b" is definitely not part of the set present in the array 202. However, if all the bits corresponding to the element "b" have the value "1", then there is a probability that the element "b" is wrongly interpreted as part of the set. This is called a probability of false positives. As such, a Bloom filter provides 0% probability for a false negative, i.e., when any element is not part of the set. However, there is a non-zero probability of a false positive. In order to ensure that the probability of false positives is acceptable, values of "m" (the number of bits in the array 202) and "k" (the number of hash functions) need to be appropriately selected. However, the values of "m" and "k" should also reduce computational load. An exemplary mathematical relationship is provided below for determining a probability of false positive.

Data may be hashed using hash functions, to populate different locations of a Bloom binary vector, prior to application of a Bloom filter. After inserting n keys in the Bloom filter 200 having the array 202 of "m" bits, the probability that a given bit is still "0" is obtained via Equation (1), which is independent of the distribution of the underlying data:

$$\left(1 - \frac{1}{m}\right)^{kn} \tag{1}$$

The probability of a false positive is given by Equation (2):

$$\left(1 - \left(1 - \frac{1}{m}\right)^{kn}\right)^k \approx \left(1 - e^{\frac{-kn}{m}}\right)^k \tag{2}$$

Figure 3:
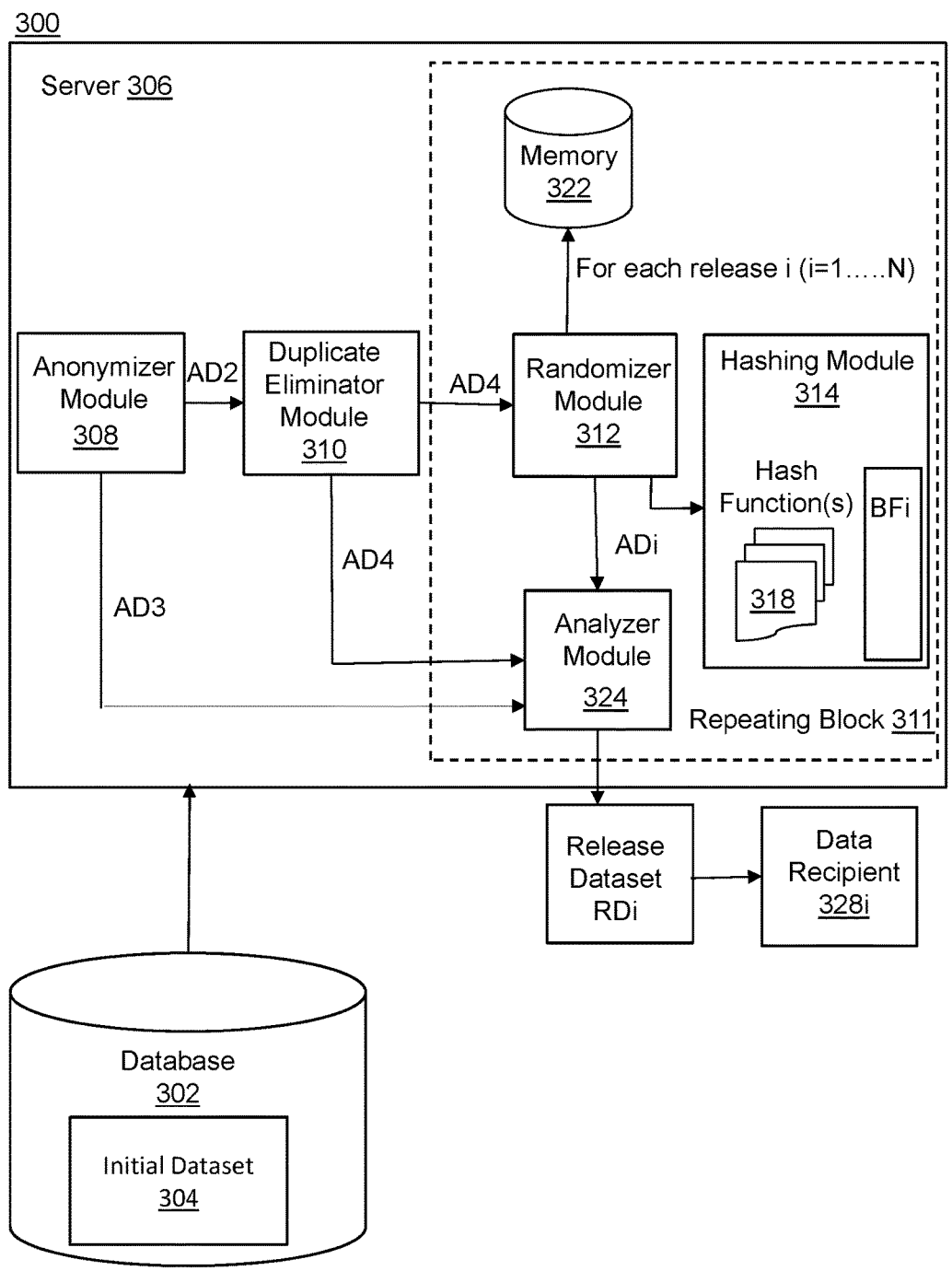
FIG. 3 illustrates a system for embedding a fingerprint, in accordance with an embodiment of the present disclosure.

FIG. 3 illustrates a system 300 for embedding a fingerprint, in accordance with an embodiment of the present disclosure. As illustrated in FIG. 3, the system 300 includes a server 306 in communicably coupled to a database 302 and a data recipient 328i.

The database 302 includes an initial dataset 304. In some embodiments, the database 302 is a computer software application that interacts with the server 306 and the data recipient 328i. In some other embodiments, the database 302 may interact with other applications and databases to capture and analyze the initial dataset 304. Further, the database 302 may be configured to perform various operations such as, but not limited to, definition, creation, querying, updating and administration of the initial dataset 304. The initial dataset 304 may include a plurality of records. Each record may include one or more fields containing information. For example, in case of a medical dataset, the record may include fields containing information of patients such as, but not limited to, name of patient, disease, length of stay, admission year, birth month, birth year and so forth. In some embodiments, each record may include a set of QI attributes and a set of non-QI attributes.

The server 306 receives the initial dataset 304 over a network (not shown). Alternatively, the database 302 may be part of the server 306. The server 306 may include various operational blocks such as, but not limited to, an anonymizer module 308, a duplicate eliminator module 310, a randomizer module 312, a hashing module 314, and an analyzer module 324. The server 306 may further include a memory 322. The memory 322 can be a dynamic memory device or a static memory device. In some other embodiments, the memory 322 may include any memory storage device such as, but not limited to, a Random Access Memory (RAM), a Read Only memory (ROM), a flash memory and so forth. In some embodiments, the memory 322 may be a cloud storage.

The anonymizer module 308 is configured to receive the initial dataset 304. The anonymizer module 308 may be implemented in software and/or hardware, and is configured to perform dataset anonymization techniques, as described herein. In some embodiments, the anonymizer module 308 may be implemented as a computer readable medium associated with a computer system or the server 306. In some embodiments, the anonymizer module 308 may be configured to perform a k-anonymity process. The k-anonymity process is used apply anonymization to the dataset in order to protect the privacy of individuals in the dataset. As a result, the k-anonymity process alters each record of the initial dataset 304 such that each record is indistinguishable from at least (k-1) other records with respect to the values of the QI attributes. In other words, at least k records would share the same QI values in the entire dataset. The k-anonymity process can be implemented via suppression and generalization.

During suppression, certain values of the attributes are replaced by some special character such as, but not limited to, asterisk "*". Further, during generalization, individual values of the attributes of the initial dataset 304 are replaced with a broader category. For example, a value "19" of an attribute "age" of the initial dataset 304 can be replaced with a range such as, 10 to 20. The QI attributes are generalized and are replaced with corresponding ranges of values. Specifically, the anonymizer module 308 replaces each QI attribute of the set of QI attributes of each record of the initial dataset 304 with a range of values to form a generalized set that satisfy k-anonymity criteria discussed above. Each generalized set therefore may include multiple ranges of values corresponding to the set of QI attributes of the respective record. Further, the range of values is based on the type of the QI attribute, an acceptable range, and domain knowledge. The result of the anonymizer module 308 is an anonymized dataset "AD1" with same number of records as the initial dataset 304. The anonymized dataset "AD1" also includes the QI attributes that are generalized in the form of the generalized sets.

The anonymizer module 308 is further configured to assign a link identifier to each record of the initial dataset 304. Alternatively, the link identifier may be part of the initial dataset 304. Each link identifier is unique for each record. In some embodiments, the anonymizer module 308 may further assign each record of the initial dataset 304 with an equivalent class (EC). EC refers to a set of k records that share the same QI values after generalization is applied. ECs are a byproduct of k-anonymization. The EC assigned to each record is based on generalized QI values, i.e., identical generalized sets are assigned with a unique EC. Therefore, each group of unique equivalent classes corresponds to a unique generalized set. In an embodiment, the anonymizer module 308 may further partition the anonymized dataset "AD1" into a first subset "AD2" and a second subset "AD3" based on the set of QI attributes and the set of non-QI attributes. Each record of the first subset "AD2" may include each generalized set representing the set of QI attributes and the corresponding link identifier. Each record of the second subset "AD3" may include the set of non-QI attributes and the corresponding link identifier. In some embodiments, the second subset "AD3" is transmitted to the analyzer module 324.

The duplicate eliminator module 310 receives the first subset "AD2" as an input. The duplicate eliminator module 310 can include hardware and/or software elements that detect and eliminate redundant and/or duplicative information from data repositories. In some embodiments, the duplicate eliminator module 310 may be implemented as a computer readable medium in association with a computer system or the server 306. In an exemplary embodiment, the duplicate eliminator module 310 removes duplicate records from the first subset "AD2" to form a de-duplicated dataset "AD4". The duplicate records are removed based on identical generalized sets that represent the QI attributes. Since each EC group have the same value for identical generalized sets, each unique EC group may represent a record in the de-duplicated dataset "AD4". In an embodiment, the duplicate eliminator module 310 removes duplicate records of the first subset "AD2" based on the EC assigned to each generalized set. Further, the duplicate eliminator module 310 retains the link identifier for each record of the first subset "AD2" to relate each record of the de-duplicated dataset "AD4" with the corresponding record of the second subset "AD3" including the set of non-QI attributes and the corresponding link identifier. Due to de-duplication, each record of the de-duplicated dataset "AD4" may have multiple link identifiers. Therefore, each EC group of the de-duplicated dataset "AD4" is associated with one or more link identifiers. The de-duplicated dataset "AD4" is transmitted to the randomizer module 312.

The randomizer module 312 can include hardware and/or software elements that generate a set of random values corresponding to an input set. In an embodiment, the randomizer module 312 may be implemented as a computer readable medium in association with a computer system or the server 306. The randomizer module 312 is configured to generate a set of random values corresponding to generalized QI attributes of each record of the de-duplicated set "AD4". Specifically, the randomizer module 312 generates a set of random values corresponding to the generalized set of QI attributes of each de-duplicated record of the de-duplicated set "AD4". Further, each random value lies within the range of values corresponding to each generalized QI attribute of each de-duplicated record.

The randomizer module 312 is further configured to generate a randomized record by replacing the generalized set of QI attributes of each de-duplicated record with the corresponding set of random values. Further, each randomized record may include one or more link identifiers corresponding to one or more records of the second subset "AD3". Specifically, the link identifiers corresponding to each EC group after de-duplication is included in each randomized record to relate each randomized record with one or more records of the second subset "AD3". The output of the randomizer module 312 is a randomized dataset "ADi". In some embodiments, the randomized dataset "ADi" is used for embedding fingerprints. The randomized dataset "ADi" is then transmitted to the analyzer module 324.

In some embodiments, the set of random values of each randomized record of the randomized dataset "ADi" passes through a hashing module 314. The hashing module 314 can include hardware and/or software elements that maps the set of random values to a Bloom filter "BFi". The Bloom filter "BFi" may be stored in the memory 322. In some embodiments, the hashing module 314 may be implemented as a computer readable medium in association with a computer system or the server 306. The set of random values of each randomized record of the randomized dataset "ADi" passes through a plurality of hash functions 318.

Each hash function 318 generates an output corresponding to each input. The plurality of outputs of the plurality of hash functions 318 are mapped to the Bloom filter "BFi". In an embodiment, each random value of the set of random values may be passed through a separate hash function 318. In such a case, the number of hash functions 318 may be equal to the number of QI attributes in the set of QI attributes, and hence the number of random values in the set of random values. In some embodiments, the server 306 may include a plurality of Bloom filters, i.e., "BF1" to "BFn" based on the number of data recipients 328i. Specifically, the server 306 assigns a unique Bloom filter "BFi" to each data recipient 328i. The Bloom filter "BFi" may include a bit vector array. In some embodiments, all bits of the bit vector array may be initially set to a value "0". Further, each of the hash functions 318 may generate an index or a position in the bit vector array upon receiving each set of random values as an input. Therefore, the output of each hash function 318 is indicative of a position in the bit vector array. Based on the output, the hashing module 314 may set the bit at the corresponding index or position of the bit vector array to a value "1". For example, if the hashing module 314 includes k hash functions 318, k indices are generated for each set of random values of each randomized record. Therefore, mapping the outputs of the hash functions 318 to the Bloom filter "BFi" includes setting the bit at the position or index indicated by each output of each hash function 318 to "1".

The analyzer module 324 can include hardware and/or software elements that can reconstruct a dataset from one or more datasets. In some other embodiments, the analyzer module 324 may be implemented as a computer readable medium in association with a computer system or the server 306. The analyzer module 324 associates each record of the randomized dataset "ADi" with one or more corresponding records of the second subset "AD3" based on one or more link identifiers associated with each record of the randomized set "ADi" and the link identifier of each record of the second subset "AD3". For example, a single randomized record may include multiple link identifiers due to de-duplication. Therefore, the set of random values of the randomized record is linked with the corresponding records of the second subset "AD3" that have the link identifiers of the randomized record.

The result of analyzer module 324 is a release dataset "RDi" that is anonymized and includes an embedded fingerprint. The set of randomized values of each record of the randomized subset "ADi" acts as a fingerprint and/or a watermark for the one or more corresponding records of the release dataset "RDi". In an embodiment, the set of randomized values of each record of the randomized subset "ADi" can be used interchangeably as a fingerprint and a watermark for the one or more corresponding records of the release dataset "RDi". Each record of the release dataset "RDi" therefore includes a link identifier, a set of random values that represent the anonymized QI attributes and a set of non-QI attributes that could have been retained in their original form or anonymized via suppression (replacing their values with special characters) if they were Direct Identifiers (DIs). Further, due to de-duplication, multiple records may include an identical set of random values as a fingerprint and/or a watermark. The release dataset "RDi" is then released to a data recipient 328i. In general, a given release dataset is associated with a particular data recipient since each recipient is supposed to be associated with a specific copy of the release dataset. Some embodiments may anonymize a set of non-quasi-identifier attributes of each record if the respective attribute is a direct identifier. For these attributes, anonymization is achieved via suppression, i.e., replacing their values with special characters. If the attribute is neither a quasi-identifier, nor a direct-identifier, it may be retained in its original format.

In an embodiment, the system 300 transmit a plurality of release datasets "RDi" for the plurality of data recipients 328i. The index "i" may be any integer equal to or greater than 2. Further, the system 300 may generate a separate release dataset "RDi" for each data recipient 328i. In an embodiment, the memory 322 may store various information related to each data recipient 328i. Such information may include contact information, name, physical address of a computer system corresponding to each data recipient 328i, and so forth. The server 306 may transmit the release dataset "RDi" to the corresponding data recipient 328i based on the information stored in the memory 322. For example, the server 306 may transmit an email or a notification to the data recipient 328i that includes details for accessing the release dataset "RDi". The server 306 may store the release dataset "RDi" on the memory 322 so that the data recipient 328i may be able to access the release dataset "RDi". In another embodiment, the server 306 may transmit the release dataset "RDi" to the data recipient 328i over a network.

In an embodiment, the anonymizer module 308 and the duplicate eliminator module 310 may carry out the anonymization and de-duplication on the initial dataset 304 only once. Therefore, for each initial dataset, the anonymization process and the de-duplication process is carried out only once. Moreover, the server 306 may store the second subset "AD3" and the de-duplicated set "AD4" in the memory 322. The randomizer module 312, the hashing module 314 and the analyzer module 324 executes their corresponding processes each time a release dataset "RDi" is to be released to the corresponding data recipient 328i. Therefore, the randomizer module 312, the hashing module 314 and the analyzer module 324 form part of a repeating block 311 of the server 306.

Before each release of a release dataset "RDi", the randomizer module 312 generates a separate set of random values corresponding to each generalized set of each de-duplicated record. Therefore, each generalized set of QI attributes is replaced by a corresponding set of random values during each release of a release dataset "RDi". Consequently, the randomized dataset "ADi" is unique for each data recipient 328i. Further, the hashing module 314 maps each set of random values of each randomized record to a specific Bloom filter "BFi" corresponding to each data recipient 328i. Since the sets of random values are separately generated for each release, the Bloom filter "BFi", formed by mapping of the sets of random values, also is unique for each data recipient 328i. The server 306 may store the Bloom filter "BFi" and the randomized dataset "ADi" in the memory 322 corresponding to each data recipient 328i. In an embodiment, the server 306 may generate and maintain a recipient database (not shown) including details of each data recipient 328i and the corresponding Bloom filter "BFi" and the randomized dataset "ADi". The server 306 may store the recipient database in the memory 322. In another embodiment, each of the data recipients 328i may be required to register with the system 300. The server 306 may provide a graphical user interface (not shown) for registration. Upon registration, the server 306 may store details related to the data recipients 328i in the recipient database. Further, the server 306 may generate and release the release dataset "RDi" upon receipt of a request from the data recipient 328i. The request may include authentication details, and the type of data required. The server 306 may authenticate the request and generate the release dataset "RDi" accordingly.

The stored Bloom filter "BFi" and the randomized dataset "ADi" may also be used for verifying whether any external dataset is part of any of the released datasets "RDi" and further determining the corresponding data recipient 328i. Therefore, any unauthorized duplication, distribution and/or tampering of one or more records of any of the released datasets "RDi" can be detected by using the sets of randomized values, embedded in each of the released datasets "ADi", as unique fingerprints for each data recipient 328i.

Figure 4:
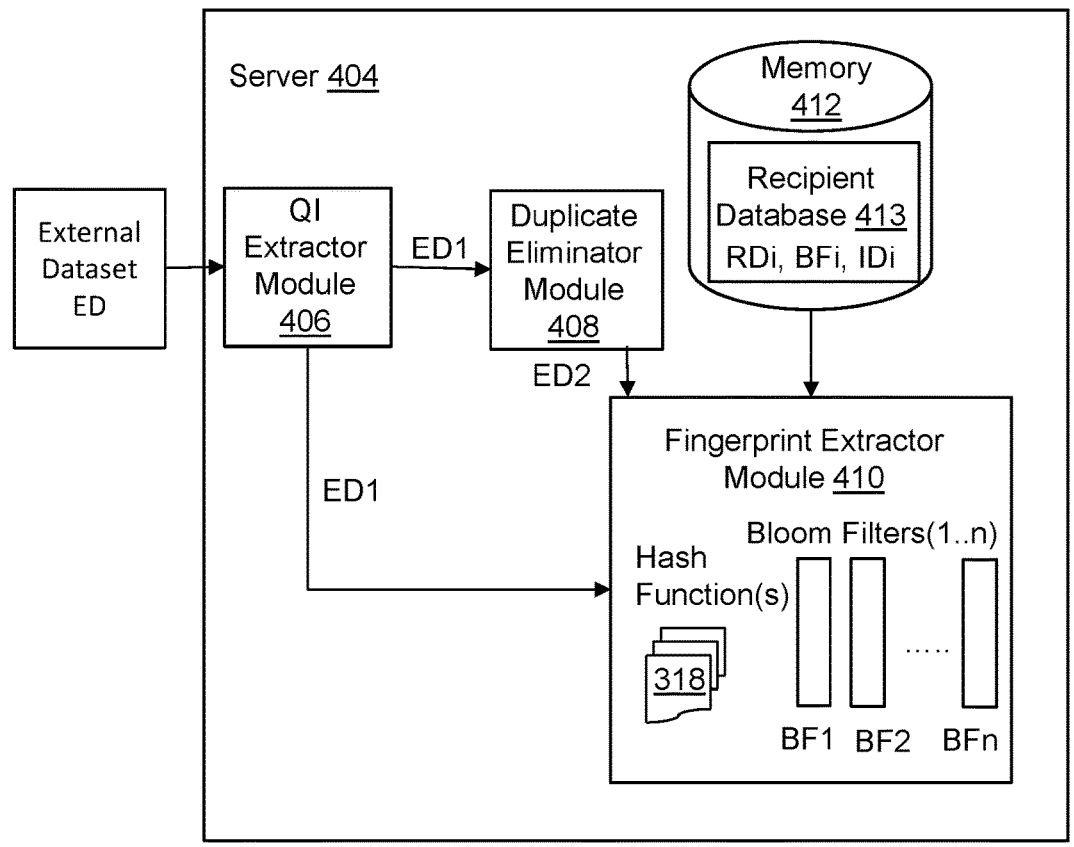
FIG. 4 illustrates a system for verifying a fingerprint, in accordance with an embodiment of the present disclosure.

FIG. 4 illustrates a system 400 for verifying a fingerprint, in accordance with an embodiment of present disclosure. A server 404 includes a QI extractor module 406, a duplicate eliminator module 408, a fingerprint extractor module 410, and a memory 412. The system 400 verifies membership of a data in a dataset stored in the memory 412.

The server 404 receives an external dataset "ED". In an embodiment, the server 404 may receive the external dataset "ED" over a network. The external dataset "ED" includes a plurality of records. Further, each record includes a set of random values and a set of non-QI attributes. In other embodiments, the set of random values of each may be associated with a set of QI attributes of the external dataset "ED". The equivalent class and more specifically, the link identifier, are used internally by embodiments. The anonymized dataset has the same number and type of fields as the original dataset. The released dataset ED does not include an EC field or a link identifier field.

The QI extractor module 406 extracts the sets of random values corresponding to the sets of QI attributes from the external dataset "ED". The QI extractor module 406 may scan each record of the external dataset "ED" and identify the set of random values of each record based on an identifier. The identifier may be stored in the memory 412. The identifier may be indicative of one or more properties of any given set of random values, for example, a length and a type of individual entries in any given set of random values. In alternative embodiments, the QI extractor module 406 may extract the sets of random values from a subset of the external dataset "ED". The subset of the external dataset "ED" may include one or more records.

In some embodiments, the QI extractor module 406 may be implemented as a computer readable medium associated with a computer system or the server 404. In some other embodiments, the QI extractor module 406 may be implemented as a hardware or software component of the server 404. The QI extractor module 406 provides a dataset "ED1" as an output. In some embodiments, the random dataset "ED1" includes only the set of random values of each record of the external dataset "ED". In other embodiments, the random dataset "ED1" may include the sets of random values of a subset of the external dataset "ED".

The duplicate eliminator module 408 receives the random dataset "ED1" as an input. The duplicate eliminator module 408 can include hardware and/or software elements that detect and eliminate redundant and/or duplicative information from a dataset. In some embodiments, the duplicate eliminator module 408 may be implemented as a computer readable medium in association with a computer system or the server 404. In an exemplary embodiment, the duplicate eliminator module 408 removes duplicate records from the random dataset "ED1" to form a de-duplicated random dataset "ED2". In some embodiments, the duplicate eliminator module 408 may remove duplicate records from the dataset "ED1" based on identical sets of random values. Therefore, the de-duplicated random dataset "ED2" includes only unique sets of random values. Further, the sets of random values in the de-duplicated random dataset "ED2" may correspond to unique sets of QI attributes.

The fingerprint extractor module 410 is configured to identify and extract information stored in the memory 412. The fingerprint extractor module 410 can include hardware and/or software elements that extract and verify records of datasets. In some embodiments, the fingerprint extractor module 410 may be implemented as a computer readable medium in association with a computer system or the server 404. In some embodiments, the fingerprint extractor module 410 extracts relevant information stored in the memory 412 to verify the membership of each record of the de-duplicated dataset "ED2" in one or more of the plurality of release datasets "RDi" (shown in FIG. 3) released to the plurality of data recipients 328i (shown in FIG. 3). Details of the generation of the release dataset "RDi" are described above with reference to FIG. 3. The information stored in the memory 412 may include information such as, but not limited to, the release datasets "RDi", details of the data recipients 328i, the corresponding Bloom filters "BFi", and so forth. In an embodiment, the memory 412 may include a recipient database 413 that includes multiple records corresponding to each of the data recipients 328i. In an example, each record of the recipient database 413 may include a data recipient identifier "IDi", the corresponding Bloom filter "BFi", and the corresponding randomized dataset "ADi". The Bloom filter "BFi" and the randomized dataset "ADi" may be generated and stored in the memory 412 during release of the release dataset "RDi" to the corresponding data recipient 328i. The memory 412 may also store the hash functions 318 that are used for mapping sets of random values of the corresponding randomized dataset "ADi" to the corresponding Bloom filter "BFi". The hash functions 318 are used during generation of the release datasets "RDi".

The fingerprint extractor module 410 may extract the Bloom filters "BFi", the hash functions 318 and the randomized datasets "ADi" from the recipient database 413 stored in the memory 412. In the illustrated embodiment, the recipient database 413 includes "n" number of records. Further, the fingerprint extractor module 410 may extract Bloom filters "BF1" to "BFn" and randomized datasets "AD1" to "ADn".

The fingerprint extractor module 410 may check one or more records of the de-duplicated random dataset "ED2" against each of the Bloom filters "BF1" to "BFn" stored in the memory 412. In some embodiments, the fingerprint extractor 410 may pass the sets of random values in one or more records of the de-duplicated random dataset "ED2" through the plurality of hash functions 318 to generate a plurality of verification outputs. The fingerprint extractor module 410 may verify that the external dataset "ED" is a part of at least one of the plurality of release datasets "RDi" released to a corresponding recipient 328i based on a comparison between the plurality of verification outputs of the plurality of hash functions 318 with one or more of the Bloom filters "BF1" to "BFn".

In an embodiment, the fingerprint extractor module 410 may verify membership of each record of the de-duplicated random dataset "ED2" with the Bloom filters "BFi" to confirm the membership of one or more records of the de-duplicated random dataset "ED2" in at least one of the release datasets "RDi". In an alternative embodiment, instead of verifying the membership of the whole de-duplicated random dataset "ED2", a subset of the de-duplicated random dataset "ED2" may be verified against the Bloom filters "BF1" to "BFn" to confirm membership of one or more of the records in at least one of the release datasets "RDi". In a further embodiment, instead of verifying the membership of the whole external dataset "ED", a subset of the external dataset "ED" is verified against the Bloom filters "BF1" to "BFn". The sets of random values of the subset of the external dataset "ED" are extracted by the QI extractor 406, de-duplicated by the duplicate eliminator module 408, and verified by the fingerprint extractor module 410, as described above. In various embodiments, the subset can be 10%, 30% or 50% of the external dataset "ED".

The fingerprint extractor module 410 compares the verification outputs of each record of the de-duplicated random dataset "ED2" against the Bloom filters "BF1" to "BFn". A verification output of each of the hash functions 318 is indicative of an index or position in a bit vector array of a corresponding Bloom filter "BFi". The fingerprint extractor module 410 checks the bit at each position of the bit vector array of the Bloom filter "BFi". If at least one bit corresponding to a record in each of the Bloom filters "BF1" to "BFn" is zero, then the record is not a member of any of the released datasets "RDi". If all the bits corresponding to a record in at least one Bloom filter "BFi" are one, then there can be three possibilities. Further, any record that is a member (all the corresponding bits are one) of a particular Bloom filter can be a potentially suspicious record.

The first possibility is that only one suspicious record is available and that a single record is a member of the Bloom filter "BFi". In the first possibility, only one record is verified as a member of only one Bloom filter "BFi".

The second possibility is that the number of available suspicious records is more than one and all the records are members of "BFi". However, some of the records may be members of other Bloom filters.

In both the first and second possibilities, provided that none of the other Bloom filters includes the suspicious record or all the suspicious records, then the data recipient 328i corresponding to the Bloom filter "BFi" is confirmed as the source of the external dataset "ED". In an embodiment, the server 404 may search for the one or more records in the randomized dataset "ADi" corresponding to the Bloom filter "BFi" to ensure that the corresponding data recipient 328i is the source of the external dataset "ED".

The third possibility is that the number of available suspicious records is one and the record is a member of more than one Bloom filter. In such a scenario, the server 404 searches for the record in the randomized datasets "ADi" corresponding to each of the Bloom filters "BFi", of which the record is a member. If the server 404 determines that the record is part of one of the randomized datasets "ADi", then the corresponding data recipient 328i is confirmed as the source of the external dataset "ED".

In case multiple records are members of multiple Bloom filters, the server 404 individually searches for each record in each of the randomized datasets "ADi" corresponding to each of the Bloom filters "BFi".

In an embodiment, the fingerprint extractor module 410 may perform fingerprint verification processes, as described above, directly on the random dataset "ED1" without any de-duplication.

FIG. 5 illustrates a dataset 500 in Table 1A. The dataset 500 may be a modified form of an initial dataset received at the server 306 (shown in FIG. 3). The dataset 500 includes four columns and ten rows. The terms "columns" and "fields" are interchangeably used hereinafter. The columns include "LINK_ID", "EC", "LOS, AYEAR, BMONTH, BYEAR" and "Non-QI attributes". The column "LINK_ID" represents link identifiers associated with each of the records of the dataset 500.

In some embodiments, a processor of the server 306 assigns a link identifier to each record. In some other embodiments, the anonymizer module 308 (shown in FIG. 3) assigns a link identifier to each record of the dataset 500. Further, the link identifier is unique for each record. In some embodiments, the link identifier distinguishes each record and establishes a connection between different fields of the dataset 500.

Each record of the column "LOS, AYEAR, BMONTH, BYEAR" may constitute a set of QI attributes and each entry of each record of the column "LOS, AYEAR, BMONTH, BYEAR" may represent an individual QI attribute. The set of QI attributes as a whole may act as a separate identifier for each record of the dataset 500, and may be used to watermark and/or fingerprint each record of the dataset 500.

As illustrated in FIG. 5, the sets of QI attributes are generalized and each QI attribute of each set is replaced with a corresponding range of values. Further, the QI attributes, i.e., LOS, AYEAR, BMONTH, and BYEAR represent length of stay, admission year, birth month and birth year, respectively, corresponding to a patient. In some embodiments, the processor of the server 306 may replace each QI attribute of the set of QI attributes of each record of the dataset 500 with the range of values. In some other embodiments, the anonymizer module 324 may replace each QI attribute of the set of QI attributes of each record of the dataset 500 with the range of values. Further, the range of values may be based on the type of corresponding QI attribute.

In dataset 500, the length of stay grouped within week intervals, the admission year is grouped within a 3-year bin, birth year is grouped within a 10-year bin and the birth month is grouped within a 6-month bin. Some of the generalized sets of QI attributes are identical, belonging to a same equivalent class (EC) represented by the column "EC". For example, the records (1, 3), (2), (4, 5, 6, 8), and (7, 9, 10) belong to EC1, EC2, EC3, and EC4, respectively. In some embodiments, the processor associated with the server 306 is configured to assign an equivalent class to each generalized set of each record of the dataset 500. In some other embodiments, the anonymizer module 324 is configured to assign an equivalent class to each generalized set of each record of the dataset 500.

The dataset 500 then is partitioned into a first subset 602 (shown in FIG. 6) and a second subset 604 (shown in FIG. 6). In some embodiments, the processor associated with the server 306 partitions the dataset 500 into the first subset 602 and the second subset 604 based on the set of QI attributes and the set of non-QI attribute. In some other embodiments, the anonymizer module 324 partitions the dataset 500 into the first subset 602 and the second subset 604 based on the set of QI attributes and the non-QI attribute.

FIG. 6 illustrates the first subset 602 and the second subset 604 in form of a Table 1B and a Table 1C, respectively. As illustrated in FIG. 6, the first subset 602 includes three columns namely "LINK_ID", "EC" and "LOS, AYEAR, BMONTH, BYEAR". The column "LOS, AYEAR, BMONTH, BYEAR" represents the set of QI attributes. Further, the second subset 604 includes two columns, i.e., "LINK_ID" and "Non-QI attributes". Each of the first subset 602 and the second subset 604 includes the link identifiers in the column "LINK_ID" in order to associate each generalized set of QI attributes with the corresponding non-QI attributes.

Further, in order to reduce time for further processing, duplicate records are removed from the first subset 602 to form a de-duplicated dataset 702 (shown in FIG. 7). The duplicate records are removed based on identical generalized sets. The identical generalized sets can be identified based on the equivalent class associated with each record. As each record of the second subset 604 is unique, the one or more link identifiers corresponding to each identical equivalent class are embedded in the de-duplicated dataset 702. In an embodiment, the processor of the server 306 may store the second subset 604 in the memory 322 of the server 306.

FIG. 7 illustrates the de-duplicated dataset 702 in Table 1D. The de-duplicated dataset 702 includes two columns and four records. The columns include "LINK_ID" and "LOS, AYEAR, BMONTH, BYEAR". The column "LINK_ID" includes link identifiers associated with each of the generalized sets of QI attributes. Due to de-duplication, some of the generalized sets of QI attributes include multiple link identifiers. The link identifiers therefore associate each generalized set of QI attributes with the corresponding one or more non-QI attributes. In some embodiments, the processor associated with the server 306 (shown in FIG. 3) removes the duplicate record from the first subset 602 (shown in FIG. 6) to form the de-duplicated dataset 702. In some other embodiments, the duplicate eliminator module 310 of the server 306 removes the duplicate records from the first subset 602 to form the de-duplicated dataset 702. The de-duplicated dataset 702 reduces the processing time and increases the efficiency of the system 300.

FIG. 8 illustrates a randomized dataset 802 in Table 1E. The randomized dataset 802 is obtained from the de-duplicated dataset 702 (shown in FIG. 7). In some embodiments, the randomized dataset 802 is generated by replacing the generalized set of QI attributes of each de-duplicated record of the de-duplicated dataset 702 with a set of random values. In some embodiments, the processor associated with the server 306 (shown in FIG. 3) generates the set of random values corresponding to the generalized set of QI attributes of each de-duplicated record. Each random value lies within the range of values corresponding to each generalized QI attribute. For example, the range (8-14) is replaced by a single value (e.g., "9") that lies within that range. In an exemplary embodiment, the generalized sets of QI attributes of the de-duplicated dataset 702 are replaced with the sets of random values such as {9,2004,4,1942}, {6,2005,10,1943}, {5,2006,3,1971}, and {2,2005,9,1960}. The sets of random values are further embedded as fingerprints and/or watermarks in a dataset 902 (shown in FIG. 9).

FIG. 9 illustrates the dataset 902 in Table 1F. In an embodiment, the dataset 902—except for the LINK_ID field—may be a release dataset that is released to a data recipient. The release dataset may include randomized values of the QI attributes, so the LINK_ID field is used to help ensure that the QI attributes after generalization, duplicate removal, and randomization are attached to the correct non-QI attributes when subset 1 and subset 2 are recombined as a release dataset. The LINK_ID field is not needed in the release dataset. Thus, by omitting the LINK_ID field from the release database, embodiments may keep the same number of columns in the release dataset without adding additional columns. For verification purposes, embodiments confirm that a dataset is or is not in the stored Bloom filters.

Embodiments use and store a unique combination of the randomized set of QI attributes generated with every release in the respected Bloom filters. During the verification process, embodiments pass the unique combination through the hash functions and determine if it exists (i.e., without false negatives) in one of the Bloom filters. This does not require storage of LINK_ID. The verification process tests whether the unique combination(s) of randomized values exist or do not exist in the Bloom filter, therefore LINK_ID is redundant and including or not including LINK_ID does not affect the verification process.

The data recipient may include any electronic device, such as a desktop computer, a portable computer, a smartphone, a tablet computer, a wearable device, and the like. In some embodiments, the data recipient is the client side system that requested at least a subset of the dataset 902.

In an embodiment, the dataset 902 is obtained from the randomized dataset 802 (shown in FIG. 8) and the dataset 500 (shown in FIG. 5). In another embodiment, the dataset 902 is reconstructed from the randomized dataset 802 (shown in FIG. 8) and the second subset 604 (shown in FIG. 6). In one embodiment, the processor of the server 306 (shown in FIG. 3) reconstructs the dataset 902 by retrieving the second subset 604 from the memory 322 and merges the randomized dataset 802 with the second subset 604 based on the link identifiers. In another embodiment, the analyzer module 324 of the server 306 (shown in FIG. 3) reconstructs the dataset 902 by retrieving the second subset 604 from the memory 322 and merges the randomized dataset 802 with the second subset 604 based on the link identifiers.

The dataset 902 may include an equal number of rows as the dataset 500. The dataset 902 includes "LOS, AYEAR, BMONTH, BYEAR", and "Non-QI attributes". LINK ID is used internally and is not released. The dataset 902 includes a set of random values for each generalized set of QI attributes. Since some of the sets of random values are associated with multiple link identifiers due to de-duplication, multiple Non-QI attributes may be associated with a single set of random values. For example, the Non-QI attributes corresponding to link identifiers 1 and 3 share the same set of random values, i.e., {9,2006,4,1942}. The sets of random values act as fingerprints and/or watermarks for each record of the dataset 902. Further, since the randomized dataset 802 is generated separately for each data recipient, the sets of random values act as unique fingerprints for each data recipient.

Figure 10:
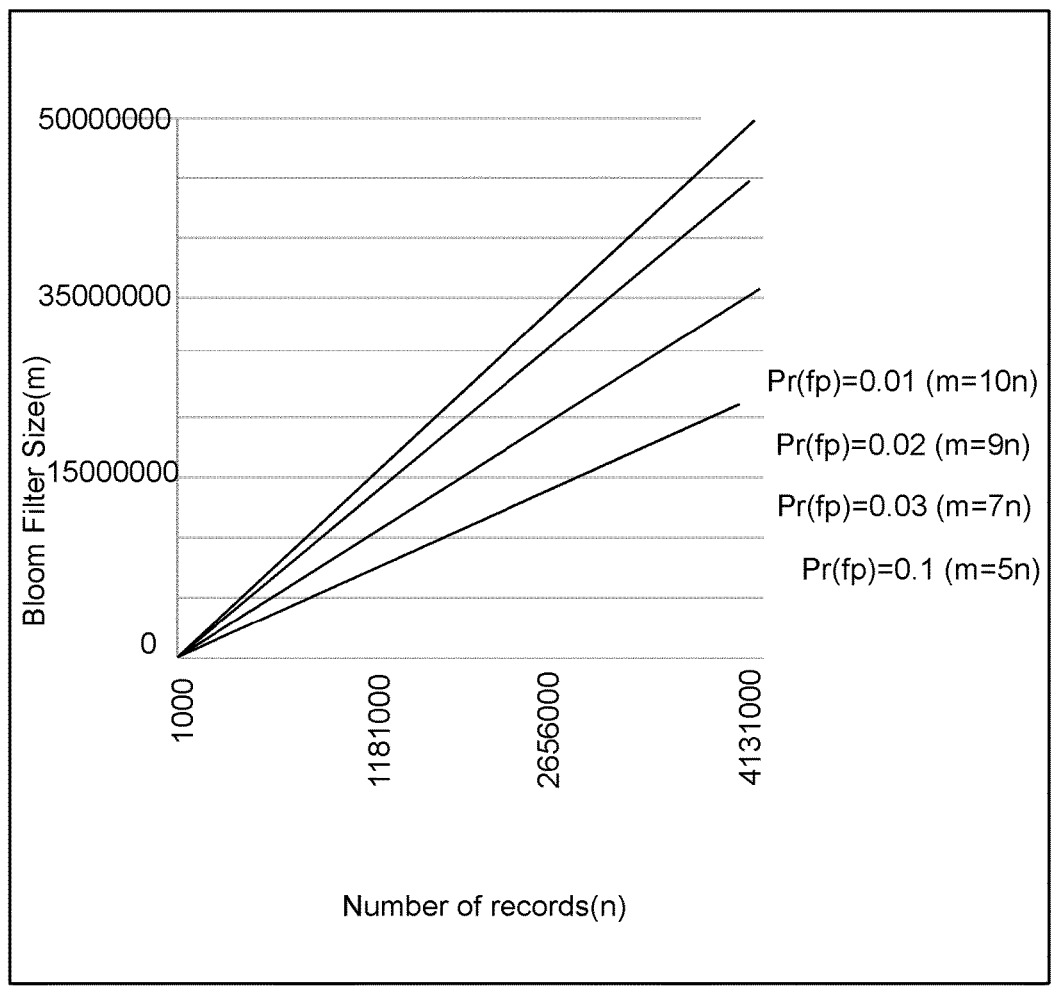
FIG. 10 illustrates a plot of Bloom filter size versus number of records, in accordance with an embodiment of the present disclosure.

FIG. 10 illustrates a plot 1000 illustrating variation of a size (m) of a Bloom filter versus number (n) of records. Usage of the Bloom filter is to test a series of messages sequentially to confirm the membership of the series of messages in a given set of messages. In an embodiment, the Bloom filter is used to check the membership of relational data records.

In an exemplary embodiment, an original or initial dataset undergoes generalization and anonymization. Each copy is anonymized according to a given pattern with respect to Quasi-Identifier (QI) attributes. Finally, each data recipient receives a copy of the dataset that is anonymized based on a given pattern. The records in each copy needs to be hashed using the Bloom filter. In other words, there is a Bloom filter associated with each copy of the anonymized dataset.

Given the probability of false positives obtained via Equation (2), a relation between the size of the Bloom filter and the number of records can be found. In this formula "k", "n", and "m" refer to the number of hash functions, the number of records, and the Bloom filter size, respectively.

The configuration of the Bloom filter ensures that false-negatives are not allowed, i.e., there is a 100% recall. In other words, the Bloom filter allows the system 400 (shown in FIG. 4) to determine if a record is a non-member with 100% certainly. However, false positives are allowed. As a result, a given record can be falsely identified as a member due to the allowable error imposed by the Bloom filter.

In an exemplary embodiment, the value of "k" is taken as 5, i.e., five hash functions are used. Further, the desired probability of false positive Pr(fp)=0.01. Based on these factors, the plot 1000 is generated by plotting the size of the Bloom filter against the number of records. Other values of Pr(fp) are also illustrated for the purpose of comparison. The results, as illustrated in FIG. 10, also correspond to the assumption in which only one suspicious record is available.

As can deduced from FIG. 10, satisfying the probability of false positive of 0.01 requires having a Bloom filter with a size ten times larger than the number of records that are hashed. Even if we increase the value of "k", obtaining (m/n<10) may not be applicable. A (m/n) ratio of 10 is practical, as can be seen from the example below.

In an example, assuming that the database consists of 5 million records ($5 \times 10^6$), a Bloom filter of 1 Kilobytes can store 1024 binary elements (either 1 or 0). With the assumption of m=10n, a Bloom filter that can store 50 million binary elements is required, i.e., $50 \times 10^6 / 1024 = 48,828.125 \times 10^3$ Bytes~$49 \times 10^6$ Bytes=49 Megabytes. Further, there can be 100,000 releases of the dataset where each release is associated with a Bloom filter of size 49 Megabytes. In order to store these Bloom filters, a space of $49 \times 10^6 \times 10^5$ Bytes=4.9 Terabytes is required. Such a space can be easily associated or coupled with a server or any data processing apparatus. Furthermore, due to the very definition of Bloom filters, lookup effort is independent of the size of Bloom filter.

As described above, a probability of false positives for a given record r1 is obtained via Equation (2). This is the case when only a single record is available for fingerprint verification. Typically, a subset of suspicious records is verified. The probability of false positive for another record r2 is once again obtained using the above formula provided that the record is not a duplicate. The resulting probability of false positive is fpr(r1)*fpr(r2). This is the probability of incorrectly identifying both records as a member. This has an important implication that the probability of false positives decrease with an increase in the number of verified records. After checking "x" records, the overall probability of false positive is obtained by Equation (3):

$$\approx \prod_{i=1}^{x} \left(1 - e^{\frac{-kn}{m}}\right)^k \approx \left(1 - e^{\frac{-kn}{m}}\right)^{kx} \Big| x \leq n \quad (3)$$

Figure 11:
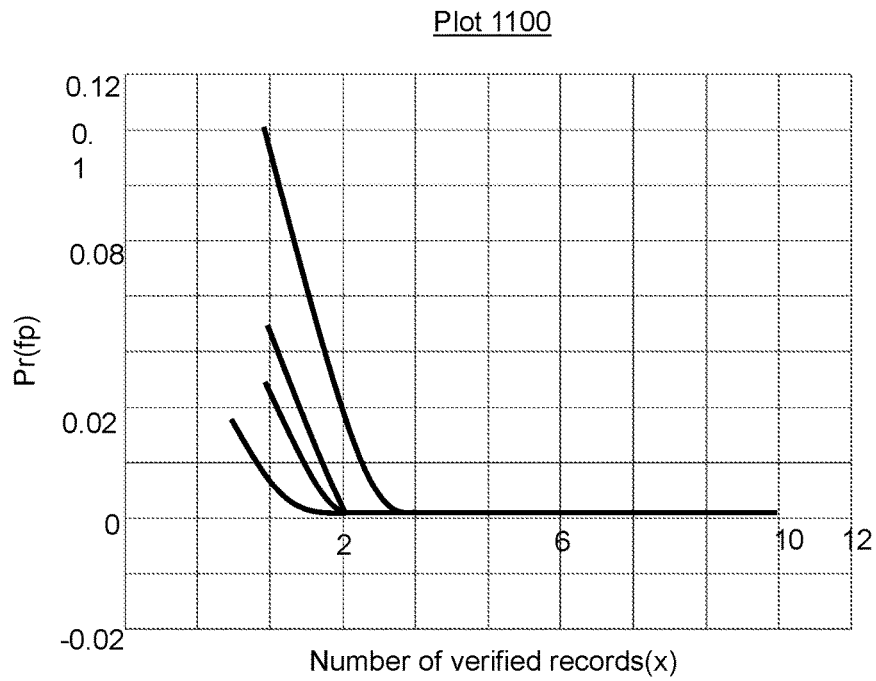
FIG. 11 illustrates a plot of probability of false positive versus number of verified records and a corresponding table, in accordance with an embodiment of the present disclosure.

FIG. 11 illustrates the relation between the probability of false positive Pr(fp) and number of releases for different Pr(fp) values. The example includes the assumptions that (m/n)=10 and k=5. As shown in a Table 11 and a plot 1100 of FIG. 11, Pr(fp) decreases with an increase in the number of available records.

Assuming that acceptable probability of false positive is 0.01, the first record is checked with the conclusion that the record is a member with 99% probably. In other words, there is only 1% probability that the record is classified incorrectly as a member.

If a subset of records is available to be verified, a second record is checked. Therefore, it can be concluded with 99.99% confidence that the two records are true members. In other words, there is only 0.01% probability that both records are incorrectly classified as members. Checking a third record will increase the certainty to 99.999, and so on.

Therefore, additional records can be used to eliminate the false positives completely. If out of two available records, the first one is a false positive and the second is a non-member, then it can be concluded that none of the records are members.

The number of records available for verification may directly impact the acceptable (m/n) ratio. Referring gain to FIG. 10, if it is known beforehand that there will be at least two records available for verification, it may be possible to reduce the size of the Bloom filter. Rather than needing a Bloom filters size that is 10 times the number of records, a (m/n) ratio of 5 (i.e., m=5n) can be used instead. When m=5n, for a single suspicious record, Pr(fp)=0.1. With a second record available, probability of false positive of both records becomes 0.01, which satisfies the requirement illustrated in FIG. 11. Similar conclusions can be made for the case of Pr(fp)=0.02 (corresponding to m=9n) and 0.03 (corresponding to m=7n) as checking more records reduces the probability of false positives significantly.

Figure 12:
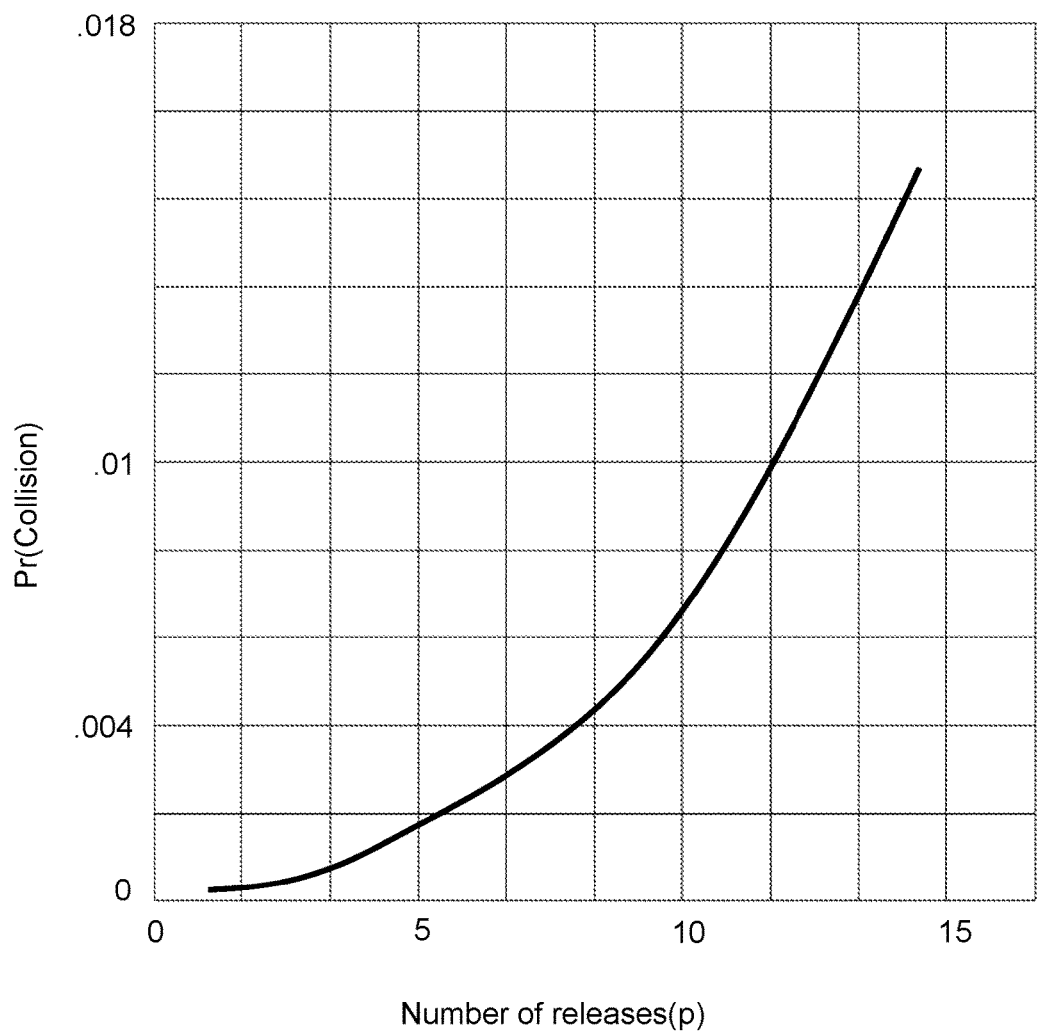
FIG. 12 illustrates a plot of probability of collision versus number of releases, in accordance with an embodiment of the present disclosure.

FIG. 12 illustrates a plot 1200 showing the relation between the probability of collision and the number of releases of a release dataset. The relation between the number of releases and the probability of collision is obtained as follows. Initially, maximum possible unique datasets that can be released is verified. Further, a number of unique generalized records is identified. Then, the number of unique generalized records are multiplied with a number of all combination of values in any of the unique generalized records.

For example, a set of QI attributes are generalized into ranges [A-B], [C-D], [E-F]. Further, the range of [A-B] includes 5 values. The range of [C-D] and [E-F] includes 3 and 7 values respectively. Randomization of the generalized set of QI attributes may provide a total of (5)*(3)*(7)=105 combinations. If the total unique number of records in the generalized dataset is 100, the number of unique datasets is obtained by multiplying the number of all combination of values with the unique number of records in the generalized dataset, i.e., 105*100=10500.

In an embodiment, some alterations are made to Equation (4) to obtain an expected number of collisions in a hash table. The alteration in Equation (4) results in Equation (5).

$$E(\text{collisions}) = p - E(\text{occupied locations}) = p - q + E(\text{empty locations}) \quad (4)$$

The expected number of collision obtained for hashing p times a given released dataset, into a hash table with q locations, is obtained from Equation (5):

$$E(\text{collisions}) = p - q + q(1 - 1/q)^p \quad (5)$$

The probability of collision will increase as the number of released datasets increases. Further, the fingerprints, according to the disclosure, depend on the intrinsic nature of the dataset. Therefore, the goal is to minimize the collision rate, while being able to generate and release a required number of datasets.

An empirical study was conducted on two databases, referenced here as Database A ("DBA") and Database B ("DBB"). Each of the two databases covered a distinct and nonover-lapping geographic region. DBA included 4,012,774 records, and DBB included 2,608,615 records. The quasi-identifier (QI) attributes associated with both DBA and DBB are listed in a Table 13A of FIG. 13. Further, a generalized hierarchy for the QI attributes is illustrated in Table 13B of FIG. 13.

According to Equation (2), for a false positive rate of 0.01, and a value of k=5, a Bloom filter of size of 10n was required for DBA, where "n" is the number of records. In this case, the number of unique generalization records were 486 and 4265 for DBA and DBB, respectively. Therefore, a Bloom filter of size 4860 bits was required. The Bloom filters associated with each of DBA and DBB are referred to as DBA_BF and DBB_RF, respectively. Therefore, for a single release of DBA, a total of 4860/1024≈4.75 Mbytes memory was required to store DBA_BF, while for a single release of DBB, a total of 42650/1024≈41.7 Mbytes memory was required to store DBB_BF.

Since each release of a dataset is associated with a separate Bloom filter, for a release of 100 datasets, one hundred DBA_BF, i.e., DBA_BF1 to DBA_BF100, required 475 MB of memory storage, while one hundred DBB_BF, i.e., DBB_BF1 to DBB_BF100, required 4.17 GB of memory storage. Further, an overall risk threshold of 0.075 was selected in order to generalize the original datasets.

Figure 14:
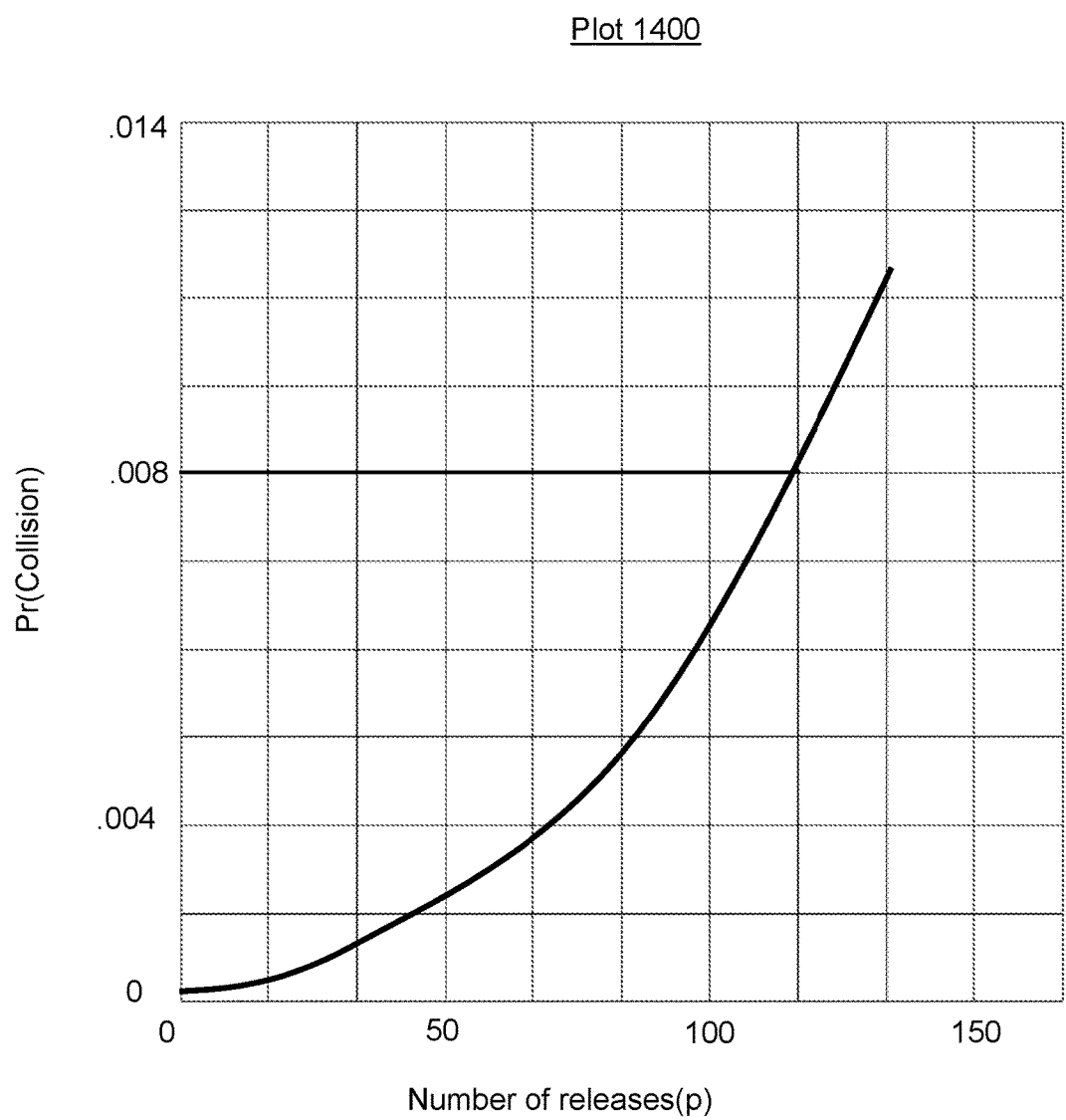
FIG. 14 illustrates a plot of probability of collision versus number of releases, in accordance with an embodiment of the present disclosure.

FIG. 14 illustrates a plot 1400 showing a relation between the number of releases with the probability of collision Pr(collision) for DBA. The original DBA dataset included 4,012,774 records. Further, the records with missing values were removed and a total of 3,793,557 records were obtained. After generalizing DBA and removal of the duplicate records from DBA, the number of unique combinations became 468 records. The unique combination of records was randomized on each new release and the resulting dataset was used for fingerprint embedding/verification purposes.

A maximum number of unique releases were identified by multiplying the number of unique combinations, i.e., 468 records with a number of all possible combinations of the generalization sets, i.e., (7)*(6)*(10)*(3)=1260*(486)=612,360. This yielded the total number of unique datasets that could have been released. Further, each unique dataset could have included at least one record that was not a part of any other released dataset. Based on Equation (4) and Equation (5), the probability of collision Pr(Collision) was obtained as 0.008. This is further illustrated in the plot 1400 of FIG. 14.

In an example, the probability of collision Pr(Collision) was reduced by selecting a smaller generalization levels to obtain larger counts. In another example, the number of QI attributes was increased by moving some of the non-QI attributes into QI category to reduce the probability of collisions, Pr(Collision).

Further, to verify the membership of one or more records, the verification system 400 (shown in FIG. 4) was executed. The results of verifying multiple releases are shown in Table 15A, as shown in FIG. 15.

For the selection of Bloom filter size and number of hash functions, a false positive rate of 0.01 for a single record was selected, resulting in a probability of falsely verifying two records together as members being (0.01)*(0.01)=0.0001. Therefore, there was a 0.0001 probability that two records were simultaneously and falsely verified as members. The set of random values, {20, 2004, 7, 2006} in Table 15A are exemplary. Although this record was in two Bloom filters in the 100 releases, the possibility of false positive was eliminated when another record, i.e., {19,2004,4,1988} was considered and when both of the records were verified simultaneously. In such a case, the two records were found, as expected, in only the Bloom filter designated as DBA_BF35.

In another example, two records were used for verification process. However, any number of records could have been used for the verification process. In another example, different portions of the release dataset were verified, corresponding to, e.g., 1%, 5%, 10%, 20%, 30%, 50%, 80%, and 100% of the release dataset. For example, with the exception of the DBA_AD25 dataset, at most 4 of the 468 records (in case of verification of 100% of the records) were found as members of other Bloom filters, namely, DBA_BF10 and DBA_BF22. The number of verified records was even fewer when a smaller portion of the dataset was available for verification. Regardless of the available portion of a subset to be verified, the membership of all records in DBA_AD25 appeared in its corresponding Bloom filter, i.e., DBA_BF25.

The time required to randomize, embed, and verify datasets is shown in Table 15B of FIG. 15. Further, the watermarking and/or fingerprinting process became feasible when large datasets are used.

Figure 16:
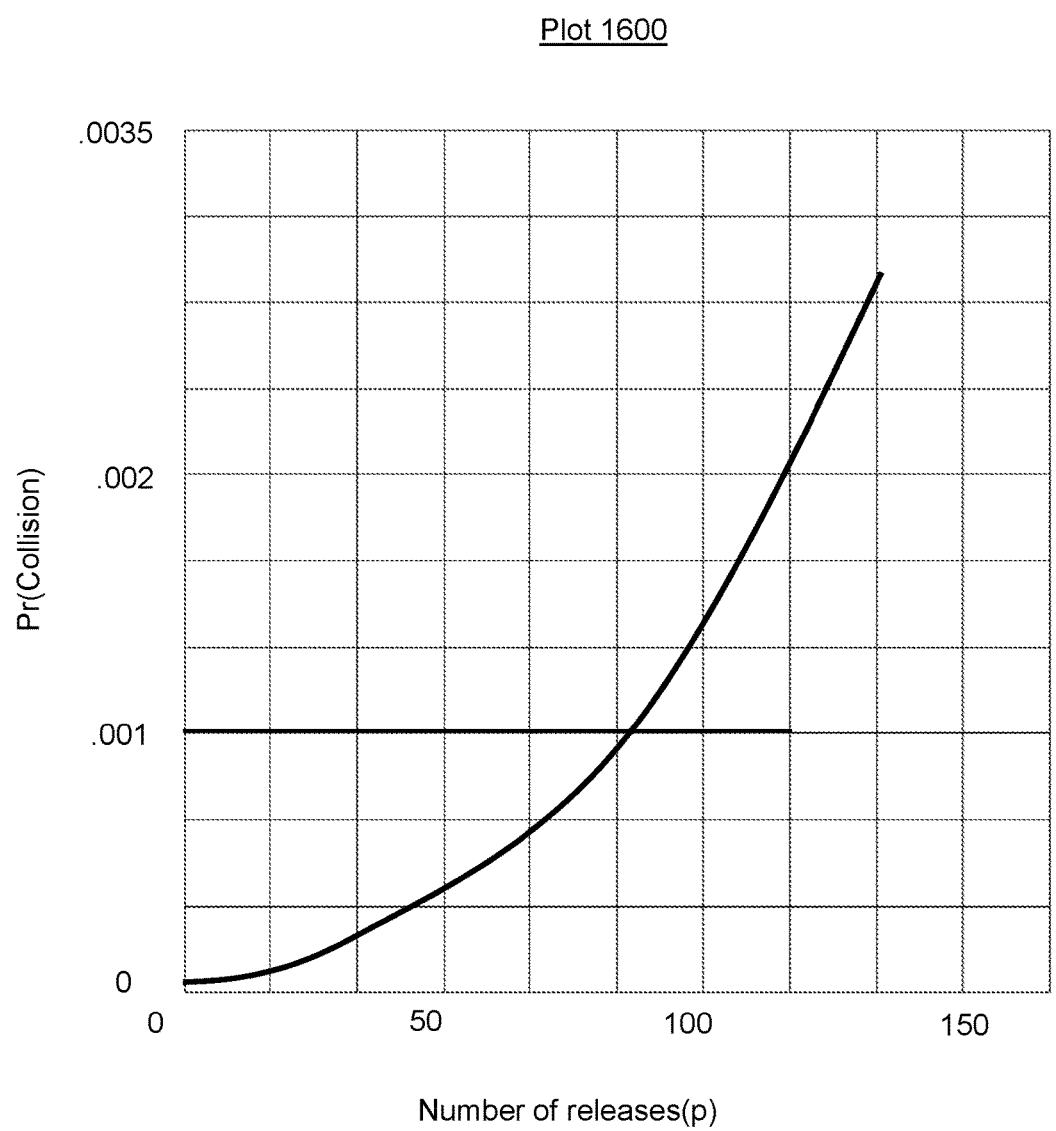
FIG. 16 illustrates a plot of probability of collision versus number of releases, in accordance with another embodiment of the present disclosure.

FIG. 16 illustrates a plot 1600, showing the relationship between the number of releases and the probability of the collision Pr (Collision) of DBB. DBB included 2,608,615 records. After removing records with missing values, 2,412,720 records were obtained. The number of unique generalized values was 4256. The number of unique generalization was larger than DBA since DBB included an additional QI attribute, i.e., ZIP code.

The maximum number of unique datasets may be 5,373,900. After 100 releases, Pr(Collision) is 0.0008 which is different from DBA due to the additional QI attribute, i.e., the ZIP code in DBB.

Further, the membership of one or more records extracted from some of the released datasets was verified. The results are shown in Table 17A of FIG. 17.

Furthermore, the membership of one of the releases DBB_AD50 in the 100 Bloom filters used 1%, 5%, 10%, 20%, 30%, 50%, 80%, and 100% of the records. Further, even in the best case, 19/4256=0.0047 or only membership of 0.47% of the records was verified in another Bloom filter.

The time required for performing different processes including embedding is shown in Table 17B of FIG. 17, which shows the feasibility of the approach.

For both DBA and DBB, the results were identical when the verification process was repeated with the same dataset multiple times.

In an exemplary embodiment, multiple anonymized versions of a dataset may be released to different recipients where each recipient is responsible for protecting the corresponding dataset. Each release is associated with a particular recipient.

Embodiments of present invention utilize Bloom filters for embedding and verifying fingerprints. This includes generating optimal anonymized datasets and allows for optimized verification of fingerprints.

For illustration purposes, two large real datasets are used to experimentally illustrate the feasibility of the present method. The system is capable of generating multiple releases of anonymized dataset with extremely precise verification results. The system can further detect the data recipient who is source of an external dataset with 100% accuracy and in an extremely short amount of time.

FIG. 18 illustrates a Table 18 showing an example of collusion detection. A Bloom filter associated with each release (subsequently recipient) is an effective mechanism for collusion detection. False negatives are not possible due to the configuration of a Bloom filter. A simple collusion scenario that can be detected using the system is shown in the following example. Subsets "R1" and "R2" are selected from corresponding datasets "AD1" and "AD6". A data recipient combines the subsets "R1" and "R2", and creates a new subset "Ds". Records r' and r" are in "AD1" and "AD6", respectively. Further, the records r' and r" are both present in the new subset "Ds", which can be linked to any given data recipient.

Due to the very definition of Bloom filters, it is impossible to have two records from the same dataset where one of them is a non-member of a Bloom filter that the other one is a member of. Therefore, the fingerprint embedding/verification mechanism of the present disclose can be used for the purpose of collusion detection.

Figure 19:
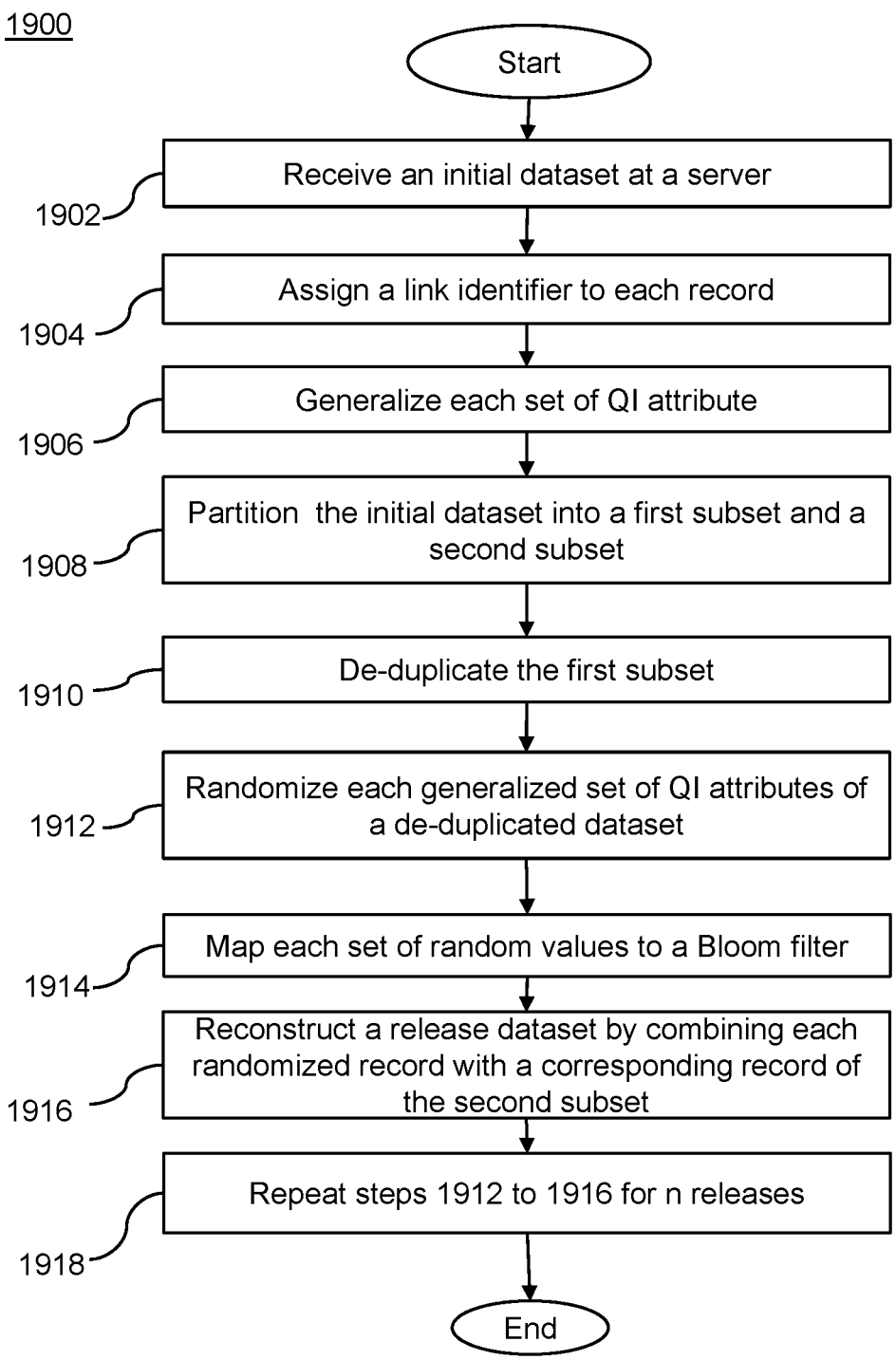
FIG. 19 illustrates a method of forming a plurality of release datasets, in accordance with an embodiment of the present disclosure.

FIG. 19 is a flowchart of a method 1700 of forming a plurality of release datasets for release to a plurality of recipients. At step 1702, an initial dataset 304 is received at the server 306 (shown in FIG. 3). The initial dataset 304 may include a plurality of records. Each record may include one or more fields containing information. For example, in case of a medical dataset, the record may include fields containing information of patients such as, but not limited to, name of patient, disease, length of stay, admission year, birth month, birth year and so forth. In some embodiments, each record may include a set of QI attributes and a set of non-QI attributes. The server 306 includes the processor 106 and the memory 108. In the initial dataset 304 may be represented by the dataset 500 shown in the Table 1A (shown in FIG. 5). In an embodiment, the processor 106 may anonymize the set of non-quasi-identifier attributes of each record using a k-anonymity privacy model process.

At step 1904, the processor 106 assigns a link identifier to each record of the dataset 503. In an exemplary embodiment, the link identifiers are incorporated in the column "LINK_ID" of the Table 1A. In some other embodiments, the anonymizer module 324 (shown in FIG. 3) assigns a link identifier to each record of the dataset 500. Further, the link identifier is unique for each record. In some embodiments, the link identifier distinguishes each record and establishes a connection between different fields of the dataset 500.

Next at step 1906, the processor 106 generalizes each set of QI attributes of each record of the dataset 500. As illustrated in FIG. 5, the processor 106 replaces each QI attribute of the set of QI attributes represented by the column "LOS,AYEAR,BMONTH,BYEAR" of each record with a range of values to form a generalized set. Further, the QI attributes, i.e., LOS, AYEAR, BMONTH, and BYEAR represent length of stay, admission year, birth month and birth year, respectively, corresponding to a patient. In some other embodiments, the anonymizer module 324 may replace each QI attribute of the set of QI attributes of each record of the dataset 500 with the range of values. Further, the range of values is based on the type of corresponding QI attribute. In the illustrated dataset 500, the length of stay is grouped within week intervals, the admission year is grouped within a 3-year bin, birth year is grouped within a 10-year bin and the birth month is grouped within a 6-month bin. As illustrated in FIG. 5, some of the generalized set of QI attributes are identical. The identical sets of generalized QI attributes belong to a same and unique equivalent class (EC) represented by the column "EC". For example, the records (1, 3), (2), (4, 5, 6, 8), and (7, 9, 10) belong to EC1, EC2, EC3, and EC4, respectively. In some embodiments, the processor 106 assigns an equivalent class to each generalized set of each record of the dataset 500. In some other embodiments, the anonymizer module 324 is configured to assign an equivalent class to each generalized set of each record of the dataset 500.

At step 1908, the processor 106 partitions the dataset 500 into the first subset 602 (shown in FIG. 6) and the second subset 604 (shown in FIG. 6) based on the set of QI attributes and the set of non-QI attribute. In some other embodiments, the anonymizer module 324 partitions the dataset 500 into the first subset 602 and the second subset 604 based on the set of QI attributes and the non-QI attribute. The first subset 602 includes the generalized sets of the QI attributes representing the sets of QI attributes and the corresponding link identifier. Further, the second subset 604 includes the sets of non-QI attributes and the corresponding link identifiers. Each of the first subset 602 and the second subset 604 includes the link identifiers in the column "LINK_ID" so as to associate each generalized set of QI attributes with the corresponding non-QI attributes. The processor 106 may store the second subset 604 in the memory 108 of the server 104.

Next at step 1910, the processor 106 de-duplicates the first subset 602 by removing duplicate records from the first subset 602 to generate a plurality of de-duplicate records. The de-duplicated records constitute a part of the de-duplicate dataset 702 (shown in FIG. 7). In some other embodiments, the duplicate eliminator module 310 of the server 306 removes the duplicate records from the first subset 602 to form the de-duplicated dataset 702. The duplicate records are removed based on identical generalized sets. The identical generalized sets can be identified based on the equivalent class associated with each record. In an embodiment, duplicate records of the first subset may be removed based on the equivalent class assigned to each generalized set. As each record of the second subset 604 is unique, the one or more link identifiers corresponding to each identical equivalent class are embedded in the de-duplicated dataset 702. In an embodiment, the processor 106 may store the second subset 604 in the memory 108 of the server 104. In an exemplary embodiment, the de-duplicated dataset 702 includes two columns and four records. The columns include "LINK_ID" and "LOS, AYEAR, BMONTH, BYEAR". The column "LINK_ID" includes link identifiers associated with each of the generalized sets of QI attributes. Due to de-duplication, some of the generalized sets of QI attributes include multiple link identifiers. The link identifiers therefore associate each generalized set of QI attributes with the corresponding one or more non-QI attributes.

At step 1912, the processor 106 randomizes each generalized set of QI attributes of each de-duplicated record of the de-duplicated dataset 702 to form the randomized dataset 802 (shown in FIG. 8). In some embodiments, the processor 106 generates a set of random values corresponding to the generalized set of each de-duplicated record of the de-duplicated dataset 702. The processor 106 generates the randomized dataset 802 by replacing the generalized set of QI attributes of each de-duplicated record with the set of random values. Each random value lies within the range of values corresponding to each generalized QI attribute. For example, the range (8-14) is replaced by the single value "9" within that range. In an exemplary embodiment, the generalized sets of QI attributes of the de-duplicated dataset 702 are replaced with the sets of random values such as {9,2004, 4,1942}, {6,2005,10,1943}, {5,2006,3,1971}, and {2,2005, 9,1960}.

Next at step 1914, the processor 106 maps each set of random value to the Bloom filter "BFi" (shown in FIG. 3). The processor 106 passes the set of random values of each randomized record of the randomized dataset 802 through the plurality of hash functions 318 to generate a plurality of outputs or hashes. The processor 106 may store the Bloom filter "BFi" in the memory 108 of the server 104. In an embodiment, each random value of the set of random values may be passed through a separate hash function 318. In such a case, the number of hash functions 318 may be equal to the number of QI attributes in the set of QI attributes, and hence the number of random values in the set of random values. In some embodiments, the server 306 may include a plurality of Bloom filters, i.e., "BF1" to "BFn" based on the number of data recipients 328i. In an embodiment, a unique Bloom filter "BFi" is assigned to each data recipient 328i. The processor 106 may store the randomized dataset 802 in the memory 108 of the server 104.

In an embodiment, the processor 106 may initialize each bit of the Bloom filters "BF1" to "BFn" to zero. The outputs of the hash functions 318 may correspond to an index or a position of each of the Bloom filters "BF1" to "BFn". After initialization, the processor 106 may set a bit of each Bloom filter "BFi" at each of the plurality of positions indicated by the hash functions 318 to one.

At step 1916, the processor 106 reconstructs a release dataset by combining each random record of the randomized dataset 802 with one or more corresponding records of the second subset 604 based on the one or more link identifiers. In another embodiment, the analyzer module 324 of the server 306 (shown in FIG. 3) reconstructs the dataset 902 by retrieving the second subset 604 from the memory 322 and merges the randomized dataset 802 with the second subset 604 based on the link identifiers. The set of random values of each randomized record is a fingerprint for the one or more corresponding records of the release dataset.

In some embodiments, the release dataset may be represented by the dataset 902 (shown in FIG. 9). The dataset 902 includes equal number of rows as the dataset 500. The dataset 902 includes randomized set of QI attributes, e.g., "LOS, AYEAR, BMONTH, BYEAR", and "Non-QI attributes". The dataset 902 includes a set of random values for each generalized set of QI attributes.

Since some of the sets of random values are associated with multiple link identifiers due to de-duplication, multiple Non-QI attribute may be associated with a single set of random values. For example, the Non-QI attributes corresponding to link identifiers 1 and 3 share the same set of random values, i.e., {9,2006,4,1942}. The sets of random values act as fingerprints and/or watermarks for each record of the dataset 902. Further, since the randomized dataset 802 is generated separately for each data recipient, the sets of random values act as unique fingerprints for each data recipient.

At step 1918, the processor 106 repeats steps 1912 to 1916 for n releases of released datasets. The processor 106 generates a plurality of release dataset 902 for the plurality of recipients 328i. Further, the plurality of release datasets 902 are released to the plurality of recipients 328i.

Figure 20:
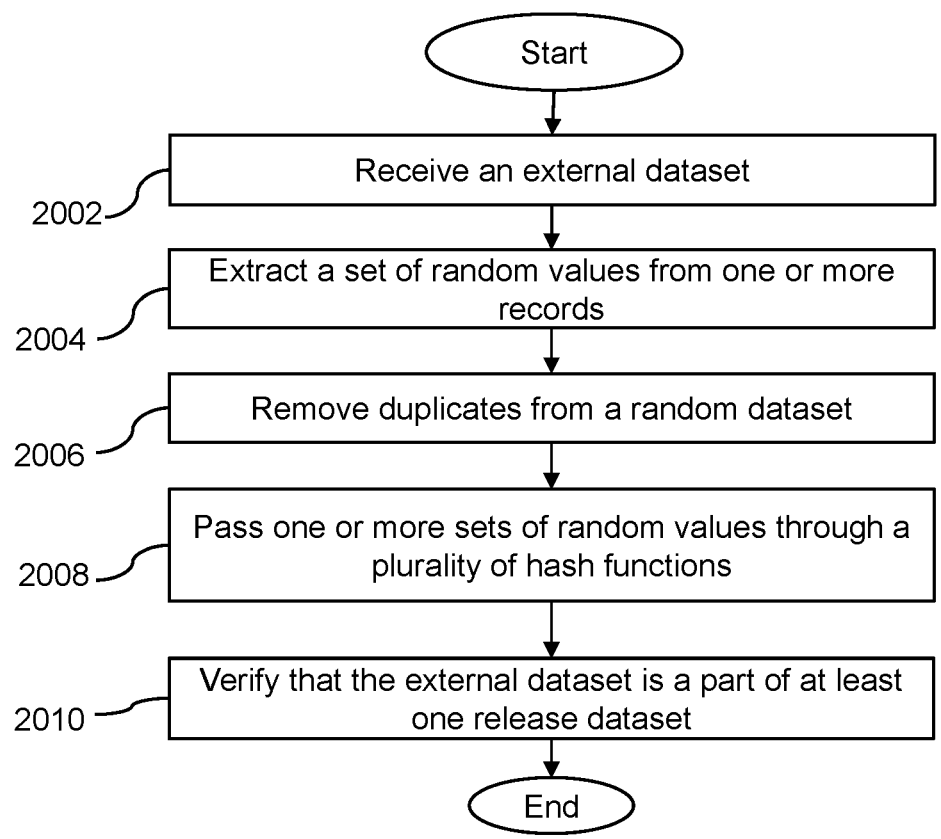
FIG. 20 illustrates a method for verifying fingerprints of a dataset, in accordance with an embodiment of the present disclosure.

FIG. 20 is a flowchart of a method 2000 for verifying whether an external dataset is a part of at least one of the release datasets. At step 2002, the processor 106 of the server 104 (shown in FIG. 1) receives the external dataset. In some embodiments, the server 104 receives an external dataset "ED" (shown in FIG. 4). In an embodiment, the server 104 may receive the external dataset "ED" over the network 110 (shown in FIG. 1). The external dataset "ED" includes a plurality of records. Further, each record includes a set of random values and a set of non-QI attributes. In some embodiments, the external dataset "ED" may include various other fields such as, but not limited to, an equivalent class field, a link identifier field and so forth. In other embodiments, the set of random values of each may be associated with a set of QI attributes of the external dataset "ED".

At step 2004, the processor 106 extracts a set of random values from one or more records of the external dataset "ED" to form the random dataset "ED1". In some embodiments, the QI extractor module 406 extracts the sets of random values corresponding to the sets of QI attributes from the external dataset "ED". The processor 106 may scan each record of the external dataset "ED" and identify the set of random values of each record based on an identifier. The identifier may be stored in the memory 108. The identifier may be indicative of one or more properties of any given set of random values, for example, a length and a type of individual entries in any given set of random values. In alternative embodiments, the processor 106 may extract the sets of random values from a subset of the external dataset "ED". The subset of the external dataset "ED" may include one or more records.

Next at step 2006, the processor 106 removes duplicate records from the random dataset "ED1" based on identical sets of random values to generate the de-duplicated dataset "ED2". In some embodiments, the duplicate eliminator module 408 (shown in FIG. 4) receives the random dataset "ED1" as an input and generates the de-duplicated dataset "ED2". The de-duplicated random dataset "ED2" includes only unique sets of random values. Further, the sets of random values in the de-duplicated random dataset "ED2" may correspond to unique sets of QI attributes.

At step 2008, the processor 106 passes the set of random values of each re-duplicated record of the de-duplicated random dataset "ED2" through the plurality of hash functions 318 (shown in FIG. 4) to generate a plurality of verification outputs. In some embodiments, the fingerprint extractor module 410 passes the set of random values of each de-duplicated record of the de-duplicated random dataset "ED2" through the plurality of hash functions 318 to generate the plurality of verification outputs. The processor 106 may check one or more records of the de-duplicated random dataset "ED2" against each of the Bloom filters "BF1" to "BFn" stored in the memory 108. The processor 106 may verify that the external dataset "ED" is at least a part of at least one of the plurality of release datasets "RDi" released to a corresponding recipient 328i based on a comparison between the plurality of verification outputs of the plurality of hash functions 318 with one or more of the Bloom filters "BF1" to "BFn".

At step 2010, the processor 106 verifies that the external dataset "ED" is part of at least one of the release datasets "RDi". In an embodiment, the fingerprint extractor module 410 may verify membership of each record of the de-duplicated random dataset "ED2" with the Bloom filters "BFi" to confirm the membership of one or more records of the de-duplicated random dataset "ED2" in at least one of the release datasets "RDi".

In an alternative embodiment, instead of verifying the membership of the whole de-duplicated random dataset "ED2", the processor 106 may verify a subset of the de-duplicated random dataset "ED2" against the Bloom filters "BF1" to "BFn" to confirm membership of one or more of the records in at least one of the release datasets "RDi". In a further embodiment, instead of verifying the membership of the whole external dataset "ED", the processor 106 may verify a subset of the external dataset "ED" against the Bloom filters "BF1" to "BFn". Further, the processor 106 may extract the sets of random values of the subset of the external dataset "ED". The processor 106 also de-duplicates the sets of random values extracted from the subset of the external dataset "ED". The processor 106 further verifies the membership of the set of de-duplicated random values in at least one of the released dataset "RDi". In various embodiments, the subset can be 10%, 30% or 50% of the external dataset "ED".

In an embodiment, the processor 106 compares the verification outputs of each record of the de-duplicated random dataset "ED2" against the Bloom filters "BF1" to "BFn". A verification output of each of the hash functions 318 is indicative of an index or position in a bit vector array of a corresponding Bloom filter "BFi". The processor 106 checks the bit at each position of the bit vector array of the Bloom filter "BFi". If at least one bit corresponding to a record in each of the Bloom filters "BF1" to "BFn" is zero, then the record is not a member of any of the released datasets "RDi". If all the bits corresponding to a record in at least one Bloom filter "BFi" are one, then there can be three possibilities. Further, any record that is a member (all the corresponding bits are one) of a particular Bloom filter can be a potentially suspicious record.

The first possibility is that only one suspicious record is available and that a single record is a member of the Bloom filter "BFi". In the first possibility, only one record is verified as a member of only one Bloom filter "BFi".

The second possibility is that the number of available suspicious records is more than one and all the records are members of "BFi". However, some of the records may be members of other Bloom filters.

In both the first and second possibilities, provided that none of the other Bloom filters includes the suspicious record or all the suspicious records, then the data recipient 328i corresponding to the Bloom filter "BFi" is confirmed as the source of the external dataset "ED". In an embodiment, the processor 106 may search for the one or more records in the randomized dataset "ADi" corresponding to the Bloom filter "BFi" to ensure that the corresponding data recipient 328i is the source of the external dataset "ED".

The third possibility is that the number of available suspicious records is one and the record is a member of more than one Bloom filter. In such a scenario, the processor 106 searches for the record in the randomized datasets "ADi" corresponding to each of the Bloom filters "BFi" of which the record is a member. If the processor 106 determines that the record is part of one of the randomized datasets "ADi", then the corresponding data recipient 328i is confirmed as the source of the external dataset "ED".

In case multiple records are members of multiple Bloom filters, the processor 106 individually searches for each record in each of the randomized datasets "ADi" corresponding to each of the Bloom filters "BFi".

Embodiments of the present invention include systems and methods that use randomized values corresponding to generalized QI attributes of a dataset as fingerprints and/or watermarks. Since generalized QI attributes are intrinsic part of the dataset, the fingerprints and/or watermarks do not add noise or impact the quality of the dataset. Thus, the utility of the dataset is not altered. Further, the randomized values can be used as watermarks and fingerprints interchangeably.

Moreover, a fingerprint is associated with each record of the dataset. Further, a Bloom filter is used for verification of the fingerprints. Therefore, due to the inherent properties of the Bloom filter, only a few records need to be checked to verify the fingerprints.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combinations.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

number of embodiments of the present disclosure have been described. While this specification contains many specific implementation details, the specific implementation details should not be construed as limitations on the scope of any disclosures or of what may be claimed, but rather as descriptions of features specific to particular embodiments of the present disclosure.

Certain features that are described in this specification in the context of separate embodiments can also be implemented in combination in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in a sequential order, or that all illustrated operations be performed, to achieve desirable results. Moreover, the separation of various system components in the embodiments described above should not be understood as requiring such separation in all embodiments, and the described program components and systems can generally be integrated together in a single software product or packaged into multiple software products.

In certain implementations, multitasking and parallel processing may be advantageous. Nevertheless, it will be understood that various modifications may be made without departing from the spirit and scope of the claimed disclosure.

What is claimed is:

1. A method to form a release dataset, the method comprising:
    receiving, at a server, an initial dataset comprising a plurality of records, each record comprising a set of quasi-identifier attributes and a set of non-quasi-identifier attributes, wherein the server comprises a processor and a memory, the processor performing the following:
    assigning a unique link identifier to each record;
    partitioning the initial dataset into a first subset and a second subset, each record of the first subset comprising a pairing of a link identifier with a quasi-identifier attribute, and each record of the second subset comprising a pairing of a link identifier with a non-quasi-identifier;
    replacing each quasi-identifier attribute with a range of values to form a generalized set;
    removing, from the first subset, duplicate records having the range of values that is identical, to generate a plurality of de-duplicated records;
    generating a random value lying within each respective range of values in the plurality of de-duplicated records;
    generating a set of randomized records by replacing the range of values in each of the de-duplicated records with the random value for the each de-duplicated record;
    hashing, with a Bloom filter, the set of randomized records to generate a hash output; and
    forming the release dataset by combining each record of the second subset with a corresponding record in the hash output that matches a respective link identifier of said each record of the second subset, wherein a set of random values of a randomized record comprises a fingerprint for the randomized record of the release dataset.

2. The method of claim 1, further comprising assigning an equivalent class to each generalized set of each record of the first subset, wherein identical generalized sets are assigned with a unique equivalent class, and wherein the duplicate records of the first subset are removed based on the equivalent class assigned to each generalized set.

3. The method of claim 1, further comprising storing the second subset, each randomized record and the Bloom filter in the memory.

4. The method of claim 1, further comprising anonymizing the set of non-quasi-identifier attributes of each record using a k-anonymity privacy process.

5. The method of claim 1, further comprising:
    receiving an external dataset comprising a plurality of records, wherein each record comprises a set of random values and a set of non-quasi identifier attributes;
    extracting the set of random values from one or more records of the external dataset to form a random dataset;
    removing duplicate records from the random dataset based on identical sets of random values to form a de-duplicated random dataset;
    passing one or more sets of random values of the de-duplicated random dataset through the plurality of hash functions to generate a plurality of verification outputs; and
    verifying that the external dataset is at least a part of the release dataset released to a recipient based on a comparison between the plurality of verification outputs of the plurality of hash functions with the Bloom filter.

6. The method of claim 5, wherein the sets of random values are extracted from a subset of the external dataset.

7. The method of claim 1, further comprising:
    initializing each bit of the Bloom filter to zero; and
    setting a bit at each of the plurality of positions corresponding to each of the plurality of outputs to one.

8. A system to form a release dataset for release to a recipient, the system comprising:
    a server comprising a processor and a memory, the server receiving an initial dataset comprising a plurality of records, each record comprising a set of quasi-identifier attributes and a set of non-quasi-identifier attributes, wherein the processor is configured to:
    assign a unique link identifier to each record;
    partition the initial dataset into a first subset and a second subset, each record of the first subset comprising a pairing of a link identifier with a quasi-identifier attribute, and each record of the second subset comprising a pairing of a link identifier with a non-quasi-identifier;
    replacing each quasi-identifier attribute with a range of values to form a generalized set;
    remove, from the first subset, duplicate records having the range of values that is identical, from the first subset to generate a plurality of de-duplicated records;
    generate a random value lying within each respective range of values in the plurality of de-duplicated records;
    generate a set of randomized records by replacing the range of values in each of the de-duplicated records with the random value for the each de-duplicated record;
    hashing, with a Bloom filter, the set of randomized records to generate a hash output; and forming the release dataset by combining each record of the second subset with a corresponding record in the hash output that matches a respective link identifier of said each record of the second subset, wherein a set of random values of a randomized record comprises a fingerprint for the randomized record of the release dataset.

9. The system of claim 8, wherein the processor is further configured to assign an equivalent class to each generalized set of each record of the first subset, wherein identical generalized sets are assigned with a unique equivalent class, and wherein the duplicate records of the first subset are removed based on the equivalent class assigned to each generalized set.

10. The system of claim 8, wherein the processor is further configured to store the second subset, each randomized record and the Bloom filter in the memory.

11. The system of claim 8, wherein the processor is further configured to anonymize the set of non-quasi-identifier attributes of each record using a k-anonymity privacy process.

12. The system of claim 8, wherein the processor is further configured to:
receive an external dataset comprising a plurality of records, wherein each record comprises a set of random values and a set of non-quasi identifier attributes;
extract the set of random values from one or more records of the external dataset to form a random dataset;
remove duplicates from the random dataset based on identical sets of random values to form a de-duplicated random dataset;
pass one or more sets of random values of the de-duplicated random dataset through the plurality of hash functions to generate a plurality of verification outputs; and
verify that the external dataset is at least a part of the release dataset released to the recipient based on a comparison between the plurality of verification outputs of the plurality of hash function with the Bloom filter.

13. The system of claim 12, wherein the sets of random values are extracted from a subset of the external dataset.

14. The system of claim 8, wherein the processor is further configured to:
initialize each bit of the Bloom filter to zero; and
set a bit at each of the plurality of positions corresponding to each of the plurality of out-puts to one.

15. A method to form a plurality of release datasets, the method comprising: receiving, at a server, an initial dataset comprising a plurality of records, each record comprising a set of quasi-identifier attributes and a set of non-quasi-identifier attributes, wherein the server comprises a processor and a memory, the processor performing the following:
(a) assigning a unique link identifier to each record;
(b) partitioning the initial dataset into a first subset and a second subset, each record of the first subset comprising a pairing of a link identifier with a quasi-identifier attribute, and each record of the second subset comprising a pairing of a link identifier with a non-quasi-identifier;
(c) replacing each quasi-identifier attribute with a range of values to form a generalized set;
(d) removing, from the first subset, duplicate records having the range of values that is identical, to generate a plurality of de-duplicated records;
(e) generating a random value lying within each respective range of values in the plurality of de-duplicated records;
(f) generating a set of randomized records by replacing the range of values in each of the de-duplicated records with the random value for the each de-duplicated record;
(g) hashing, with a Bloom filter, the set of randomized records to generate a hash output;
(h) forming a release dataset by combining each record of the second subset with a corresponding record in the hash output that matches a respective link identifier of said each record of the second subset, wherein a set of random values of a randomized record comprises a fingerprint for the randomized record of the released dataset;
(i) assigning a unique Bloom filter to the release dataset; and
(j) repeating steps (e) to (i) to generate the plurality of release datasets.

16. The method of claim 15, further comprising assigning an equivalent class to each generalized set of each record of the first subset, wherein identical generalized sets are assigned with a unique equivalent class, and wherein the duplicate records of the first subset are removed based on the equivalent class assigned to each generalized set.

17. The method of claim 15, further comprising storing the second subset, each randomized record and the Bloom filters in the memory.

18. The method of claim 15, further comprising anonymizing the set of non-quasi-identifier attributes of each record if the respective attribute is a direct identifier.

19. The method of claim 15, further comprising:
receiving an external dataset comprising a plurality of records, wherein each record comprises a set of random values and a set of non-quasi identifier attributes;
extracting the set of random values from one or more records of the external dataset to form a random dataset;
removing duplicates from the random dataset based on identical sets of random values to form a de-duplicated random dataset;
passing one or more sets of random values of the de-duplicated random dataset through the plurality of hash functions to generate a plurality of verification outputs; and
verifying that the external dataset is at least a part of at least one of the plurality of release datasets released to a corresponding recipient based on a comparison between the plurality of verification outputs of the plurality of hash functions with one or more of the Bloom filters.

20. The method of claim 15, further comprising:
initializing each bit of the Bloom filter to zero; and
setting a bit at each of the plurality of positions corresponding to each of the plurality of outputs to one.

* * * * *